(12) United States Patent
Yelken

(10) Patent No.: US 11,033,060 B1
(45) Date of Patent: *Jun. 15, 2021

(54) SOFT SILICONE EDGED CUSHION FOR FACE AND OXYGEN MASKS WITH ULTRAVIOLET LIGHT SOURCE

(71) Applicant: Aslan Medical Equipment, LLC, Baltimore, MD (US)

(72) Inventor: Suat Yelken, Baltimore, MD (US)

(73) Assignee: ASLAN MEDICAL EQUIPMENT, LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/154,874

(22) Filed: Jan. 21, 2021

Related U.S. Application Data

(63) Continuation-in-part of application No. 16/880,496, filed on May 21, 2020, now Pat. No. 10,966,471.

(Continued)

(51) Int. Cl.
*A41D 13/11* (2006.01)
*A61M 16/06* (2006.01)
(Continued)

(52) U.S. Cl.
CPC ............ *A41D 13/1146* (2013.01); *A61L 9/20* (2013.01); *A61M 16/0605* (2014.02); *A62B 9/06* (2013.01);
(Continued)

(58) Field of Classification Search
CPC .......... A61M 16/0683; A61M 16/0616; A61M 16/0605; A61M 16/0622; A61M 16/0688;
(Continued)

(56) References Cited

U.S. PATENT DOCUMENTS

| 6,681,765 B2 * | 1/2004 | Wen ....................... A62B 18/02 128/201.25 |
| 7,658,891 B1 * | 2/2010 | Barnes ..................... C01B 13/10 422/186.03 |

(Continued)

OTHER PUBLICATIONS

Trafton, Anne, "Engineers Design a Reusable Silcone Rubber Face Mask with an N95 Filter," SciTechDaily, Jul. 12, 2020, 9 pages.

(Continued)

*Primary Examiner* — Robert H Muromoto, Jr.
(74) *Attorney, Agent, or Firm* — Cameron LLP

(57) ABSTRACT

A soft medical silicone edged cushion may significantly reduce air leakage and provide comfort to a wearer of a face mask, for example, when the face mask is continually worn by a healthcare worker for a twelve hour shift of medical duty. The cushion may preferably be U-shaped and comprise a cross-section for holding an extra soft silicone gel or air, yet be sufficiently hard and elastic and of predetermined circumference to be adaptable to self-installation to the lateral edges of a face mask and coatable to protect from the escape of air and fit comfortably on a face despite the use of elastic straps with the face mask or the presence of solid plastic lateral edges of an oxygen mask or a ventilator mask. The cushion may be used to cushion a solid plastic laterally edged oxygen or ventilator mask against the use of elastic ties to tie the face mask around a patient's head. The face mask may comprise a UVC source of ultraviolet light controlled by buttons/displays/battery/USB port on the cushion or on a cartridge replacing a filter of an N95 mask.

13 Claims, 15 Drawing Sheets

Related U.S. Application Data

(60) Provisional application No. 63/027,208, filed on May 19, 2020, provisional application No. 63/131,717, filed on Dec. 29, 2020.

(51) Int. Cl.

| | | |
|---|---|---|
| *C09D 127/18* | (2006.01) | |
| *A62B 18/08* | (2006.01) | |
| *A62B 9/06* | (2006.01) | |
| *A61L 9/20* | (2006.01) | |

(52) U.S. Cl.
CPC ............ *A62B 18/08* (2013.01); *C09D 127/18* (2013.01); *A61L 2209/12* (2013.01); *A61L 2209/14* (2013.01); *A61M 2202/0208* (2013.01); *A61M 2205/3584* (2013.01); *A61M 2205/8262* (2013.01); *A62B 18/084* (2013.01)

(58) Field of Classification Search
CPC .. A61M 2205/0216; A61M 2210/0618; A61M 2209/08; A61M 2205/0266; A61M 2205/8262; A61M 2205/3584; A61M 2202/0208; G02C 11/12; G02C 3/003; G02C 2200/08; G02C 5/12; G02C 11/02; A62B 23/025; A62B 18/08; A62B 18/084; A62B 18/00; A62B 18/02; A62B 23/00; A62B 23/02; A62B 9/06; A41D 13/015; A41D 13/11; A41D 13/1176; A41D 13/1138; A41D 13/1161; A41D 13/1169; A41D 13/1192; A41D 13/0556; A41D 13/1107; A41D 13/1146; A61F 9/026; A61F 13/126; A61F 9/045; A61F 2006/042; A61F 2013/00476; A61F 2013/00578; A61F 2013/15024; A61F 2/7812; A42B 3/288; A63B 71/10; F16F 9/306; C09D 127/18; A61L 9/20; A61L 2209/12; A61L 2209/14

See application file for complete search history.

(56) References Cited

U.S. PATENT DOCUMENTS

| | | | | |
|---|---|---|---|---|
| 8,397,715 | B2 * | 3/2013 | Litz | .......................... A62B 7/10 |
| | | | | 128/201.25 |
| 9,963,611 | B2 | 5/2018 | Stewart et al. | |
| 10,834,978 | B1 * | 11/2020 | Yelken | ..................... A62B 7/00 |
| 2003/0111075 | A1 * | 6/2003 | Wen | ....................... A62B 23/02 |
| | | | | 128/201.22 |
| 2007/0102280 | A1 * | 5/2007 | Hunter | ...................... A61L 9/16 |
| | | | | 204/157.15 |
| 2009/0014002 | A1 * | 1/2009 | Krafthefer | ........... A62B 18/006 |
| | | | | 128/205.18 |
| 2010/0132715 | A1 * | 6/2010 | Litz | .......................... A61L 9/20 |
| | | | | 128/207.12 |
| 2015/0114397 | A1 * | 4/2015 | Litz | ....................... A62B 23/02 |
| | | | | 128/206.15 |
| 2018/0064968 | A1 * | 3/2018 | Taslagyan | ................ A61L 9/20 |

OTHER PUBLICATIONS

Bai et al., "Presumed Asymptomatic Carrier Transmission of COVID-19," Journal of the American Medical Association, Apr. 14, 2020, pp. 1406-1407.

Budowsky et al., "Principles of Selective Inaxctivation of Viral Genome," Archives of Virology 68, pp. 239-247, Springer-Verlag, 1981.

Narita et al., "Ultraviolet C light with wavelength of 222 nm inactivates a wide spectrum of microbial pathogens," Journal of Hospital Infection, pp. 459-467, 2020.

Ponnalya et al., "Far-UVC light prevents MRSA infection of superficial wounds in vivo," PLoS ONE 13 (2), 12 pages, 2018.

Buonanno et al., 207-nm UV Light—A Promising Safe Tool for Safe Low-Cost Reduction of Surgical Site Infections. II: In-Vivo Safety Studies, 12 pages, 2016.

Wladyslawetal, Ultraviolet Germicidal Irradiation Handbook, Immune Building Systems, Inc., Springer Heidelberg, 2009.

Trevisanetal, "unusual High Exposure to Ultraviolet-C Radiation," Photochemistry and Photobiology, American Society for Photobiology, pp. 1077-1079, 2006.

Navy Environmental Center, Ultraviolet Radiation Guide, 1992.

Naritaetal, "Chronic irradiation with 222-nm UVC light induces neither DNA damage nor epidermal lesions in mouse skin, even at high doses," PLOS ONE, pp. 1-9, 2018.

Yamanoetal, "Long-term Effects of 222-nm ultraviolet radiation C Sterilizing Lamps on Mice Susceptible to Ultraviolet Radiation," Photochemistry and Photobiology, 96, pp. 853-862, 2020.

Wooetal, "Coronavirus Genomics and Bioinformatics Analysis," Viruses, 2, pp. 1804-1820, 2010.

* cited by examiner

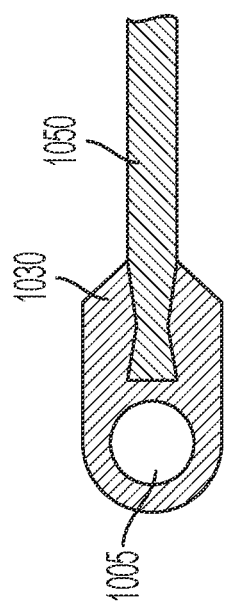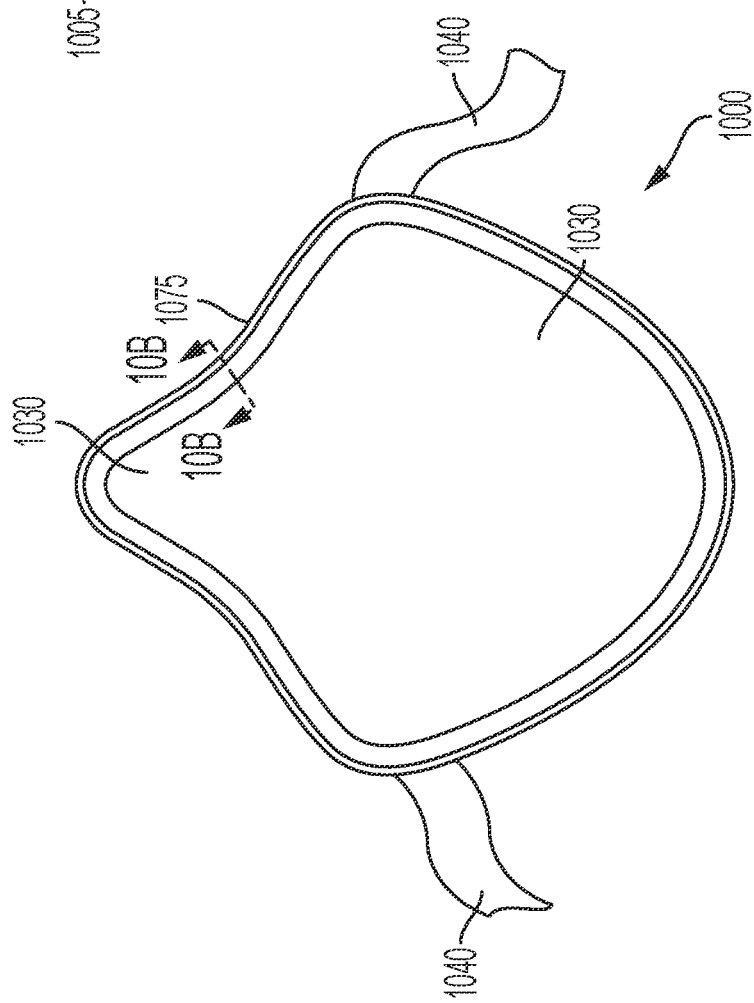

SOFT SILICONE EDGED CUSHION FOR FACE AND OXYGEN MASKS WITH ULTRAVIOLET LIGHT SOURCE

This application is a continuation-in-part of U.S. patent application Ser. No. 16/880,496 originally filed May 21, 2020 which application claims the benefit of priority to U.S. Provisional Patent Application Ser. No. 63/027,208 filed May 19, 2020, entitled "Soft Silicon Edged Cushion for Face Masks," by the same inventor, and this application claims the right of priority to provisional patent application Ser. No. 63/131,717 filed Dec. 29. 2020.

FIELD OF THE INVENTION

The present invention generally relates to the technical field of personal protection equipment (PPE) apparatus and a method for protecting the face of a healthcare worker, a patient requiring use of a ventilator or an oxygen mask, a surgeon desirous of a safe and comfortable surgical mask, or emergency technical personnel requiring protection from damage during prolonged use of a face mask and, more particularly, to apparatus comprising a semicircular, flexible U-shaped channel and access to a source of ultraviolet light. The cushion may comprise a soft medical gel or jelly material to prevent leakage, and the U-shaped channel may contain controls comprising a circuit including a battery, a USB port for charging the battery, power on/off button, a Bluetooth indicator and other devices and, likewise the PPE may include a cartridge. The cartridge may alternatively contain the controls and be located so as to extend through a face mask and operate one or a series of ultraviolet light sources and the controls may be located on the face mask with the ultraviolet sources and reachable by a wearer of a face mask. The soft gel material or a jelly may coat the U-shaped channel of the cushion contacting a user's face, and the U-shaped channel may clasp lateral edges of a cloth or plastic surface of the face mask so as to protect a user from facial damage or discomfort.

BACKGROUND OF THE INVENTION

CNN interviewed Dr. Sanjay Gupta, medical advisor to CNN, on Jul. 24, 2020. During the CNN interview, Gupta is quoted as saying: "We're basically told to reuse the same mask as long as we can." In answer to a question of an interviewer, Dr. Gupta stated: "So the mask, just not that this matters as much, but you're wearing this mask doing a five, six hour operation. If you're wearing it properly with a fit test, it digs into your face. It hurts after a while. But you do everything to protect it; it's like gold. So I'll wear another mask on top of it, to prevent that N95 mask from being contaminated."

Across the United States and internationally, local, state and federal governments are recommending the use of social distancing and related face masks to safeguard from a pandemic related to corona virus or Covid-19 and variants. Despite weeks of conflicting, and often confusing information on the effectiveness of face masks of all types for public use, the Center for Disease Control and Prevention (CDC) recommends that everyone wear face masks and practice social distancing. Personal protective equipment (PPE), which may comprise a face mask or shield, may be defined for the purposes of this patent application as any variation of a face mask or shield that is intended to cover the mouth and nose to protect against inhalation/exhalation of, or other exposure, to virus pathogens. The face mask or shield may be a surgical mask, a mask of hard rubber or plastic material (for example, an oxygen mask or a ventilator mask), a hood worn over the face or a cloth mask produced from several layers of a cloth material. One or more layers may be capable of bonding to and holding incoming pathogens and the like preventing them from being inhaled. According to the CDC, "cloth face coverings should: fit snugly but comfortably against the side of the face; be secured with ties or ear loops; include multiple layers of fabric; and allow for breathing without restriction." In particular, cloth masks are recommended for general use and surgical masks and N95 respirators manufactured, for example, by 3M since 1972 are recommended for use by healthcare workers. The N in N95 denotes a rating that does not protect against oil-based aerosols but is highly recommended for use by healthcare workers. The 95 represents the percent of 0.3 micron particles removed from air that is inhaled through the face mask.

Hospitals have also used oxygen masks or ventilators to deliver pathogen-free oxygen through the nose in acute or intensive care units. For the present purposes, an oxygen mask or a ventilator may cause problems with comfort of the mask/ventilator, and such an oxygen mask or ventilator device is encompassed by the present patent application.

People who go to public places such as grocery stores may wear disposable cloth or paper masks while healthcare workers may, for example, use N95 respirators and surgical masks. Whether one is a member of the public or a healthcare worker, a mask or shield should completely cover the mouth and nose and preclude the inhalation/exhalation of air through gaps in the cloth/paper/plastic of the mask caused by inappropriate use of the face mask or the rigidity of a mask made from solid material such as a ventilator or oxygen mask. At the same time, masks (as opposed to handkerchiefs, bandanas, make-shift face masks and shields) should be avoided because air and liquid droplets of pathogens may not be absorbed by the single layer of cloth, or blocked by a shield alone and may enter via the chin or eye area or other unprotected areas of the face.

The general public who use their masks when in the bright sunshine and wear sun-glasses or are required to wear eyeglasses to drive or ride in a vehicle will exhale warm, moist air through a cloth/paper mask and quickly learn that their eyeglasses with fog up and cause them to lose sight. Some face masks are designed to provide for wire (small gauge aluminum or copper wire, for example, insertion at the edges of a mask; some have shaped sponges for shields, for example, around the nose. These may require manipulation to avoid discomfort or escape of air toward the eyes (and so protect against foggy eyeglasses).

Many people fail to use proper masks and choose to use handkerchiefs or scarves tied behind their faces which may permit air into openings, for example, when simply tied behind one's neck and receive air, for example, or pathogens from an opening under one's chin. On the other hand, the elastic used in forcing a pre-structured oxygen or ventilator mask of hardened rubber or plastic to cover the many different shapes of faces (everyone's face is differently shaped from one another) can cause facial damage and still be ineffective in covering gaps around lateral edges of the mask in an effort to cover one's mouth and nose. If one's mask does not fit properly, one will be constantly adjusting the mask and may touch their face exposing them to a viral infection. These masks may have strong elastic ties to one's ears or around the head. When one wears such a mask for a long period of time, the elastic strength may cause irritation, rashes, markings and general discomfort around its edges.

Wearing face masks are now an important part of our everyday lives. However, wearing face masks for long periods of time can cause skin issues and irritation. Dermatologists studying the issue of lengthy use, for example, wearing the same mask all day, will irritate facial skin, clog pores, cause acne, rosacea and dermatitis. Also, healthcare workers are under a lot of stress as they go about their daily duties of, for example, intubation, inserting oxygen tubes into a nose of a Covid-19 patient or the stress of an operating room or an intensive care unit.

An N95 mask tightened onto the face puts all the pressure of, for example, a pair of strong elastic or rubber straps for tying the mask to the ears or the back of the head onto the soft facial tissue that is in contact with the mask's lateral edges, especially a mask made of hard rubber, composite paper-like material, cloth or plastic. Researchers have calculated that the resulting pressure from medical masks can be greater than an equivalent of three pounds per square inch on the face's soft tissue. A medical worker wearing such a mask all day will likely suffer from the edges of the mask and may want to be careful about choosing the shape of a mask for a twelve-hour shift.

Overly dry skin can lead to skin inflammation due to cracks and fissures while facial skin may sweat, masks may be used in humid conditions and so one's skin may be susceptible to irritation. A moisturizing cream or petroleum jelly may help some with dry skin but a moisturizing cream is not designed to prevent air from leaking from edges of a face mask.

U.S. Pat. No. 9,963,611 (the '611 patent) to Stewart et al. describes a composition (for example, of multiple layers of different types of cloth) and at least two different masks. One type of known face mask is seen in FIG. 1 and one in FIG. 2 for use as a face mask to shield against viral pathogens. The mask may comprise a lateral edge and looped with a loop extension from the lateral edges to wearing on one's ears. A top edge protects the nasal area while a larger mask body protects, the mouth and nose.

A second embodiment of a type of facial mask is shown in FIGS. 3 and 4 of the '611 patent (with a resilient member that may be a foam or deformable strip adjusted by the wearer and flap for contour about the nose), comprising components as seen in FIGS. 5, 6, 7 and especially FIG. 8. The face mask of the '611 patent may comprise a flap and sides that may be stitched together to protect the face while having to manipulate the mask to exclude pathogens from reaching the nose and mouth. As seen in FIGS. 9 through 12 of the '611 patent of Stewart et al., the mask may comprise as many as four or more layers of different absorbent materials, at least one layer for capturing and bonding to pathogens. FIGS. 1 and 2 show typical disposable face masks with loops 14 to tie the face mask to one's ears. Lateral edges 30 have a perpendicular connection to a top edge and bottom body 12. On the other hand, FIGS. 3-8 show a mask which has lateral edges which are more adaptable to being protected and include a flap 104 and a resilient member 142 for fitting above the nose bridge.

Prior art FIG. 1 of the present patent application shows a woman wearing a typical oxygen face mask comprising a plastic nose and mouth covering 100. The lateral edge of the plastic covering 100 is hard and may damage the face. The figure appears to show the use of an elastic band which surrounds the rear of her head above her ears and may help to lift and hold the tube attached to the mask which serves as an oxygen supplement. There is a plastic lateral edge 125 which, being held to the face by elastic, can cause discomfort. There also appears to be a hardened plastic nose bridge contoured to prevent oxygen from escaping to reach her eyes.

Prior art FIG. 2 shows a patient lying in a bed wearing a ventilator mask 200 which appears to comprise plastic or a hardened medical silicone or rubber. Like the oxygen mask 100, the ventilator mask 200 appears to have a hardened plastic or silicone lateral edge 225 held by elastic bands to the face of the male patient. Also, it appears from the drawing that the patient is in discomfort and may have puffy cheeks caused by long term use of the ventilator mask 200. The oxygen appears to be delivered by a tube directly to the nasal area of the patient.

Prior art FIG. 3 shows the exterior of a typical 3M N95 rated mask 300 typically worn by healthcare workers. The lateral edges 320 may be made of a stiffened cloth material and appear to be held to the face by pairs of elastic straps. Healthcare workers may wear their masks for twelve hour shifts. After twelve hours, there may be considerable discomfort from wearing the mask. Filter 315 is engineering to capture particulate matter as described above. Also, the cloth lateral edges 320 may capture air on inhalation and release air on exhalation. A healthcare worker may have a need to adjust the mask frequently due to the use of the stiffened cloth to snuggly fit over the nose and mouth.

Prior art FIG. 4 shows the interior of the 3M N95 rated mask 400. The interior includes a breathing grid 415 which is differently sized than filter 315 and also includes a foam rubber nose bridge 410. The foam rubber nose bridge 410 may cause some discomfort from a wearer's moving their head especially over a twelve-hour shift period.

From measuring the circumference of lateral edges of prior art face masks of the prior art types described above, the circumferences of prior art masks all appear to be approximately the same. As will be discussed below, the similar circumferences may be utilized to advantage in the present invention.

Personal protective equipment may comprise a shield that protects the whole body or at least one's head from a viral pathogen such as COVID 19, for example, a hood with a window or a face shield like a visor. Because a face shield may just protect the face when a wearer is close to a patient, a face shield should be used with a face mask.

Also, there is an ultraviolet invisible light source known in the art for producing a band of ultraviolet frequencies between 207 and 222 nM wavelength that inactivates a coronavirus but has no significant impact on the skin of a user's face such as causing a sunburn-like condition if used in small quantities.

There remains in the art a need to solve the problems caused using sharp-edged plastics, cloths, silicone and hardened rubber materials for a face mask with elastic rubber or string ties to the ears or surrounding the head that can cause considerable discomfort. Some forms of disease and sores may develop that cannot be treated with moisturizing cream alone. The use of deformable strips, resilient members and wires embedded in edges of cloth face masks, surgical masks or oxygen masks or ventilators may cause skin damage.

SUMMARY OF THE EMBODIMENTS

The present invention solves the comfort and protection problems of prior art personal protective equipment (PPE) including face mask and face shield designs. An embodiment of the face mask protection is designed to comprise a U-shaped cushion apparatus (a cushion that may be sized to fit the circumference of the mask) and a soft medical gel type material such as a medical silicone (Shore A0 to 10 on the hardness scale or 10-80 for firmly clasping the lateral edges of the mask) that may be fixed to the lateral edges of a face mask that may or may not contain deformable wires that a user may shape to the contours of their face or nose. From investigation, it has been determined, as indicated above, that most face masks have the same or similar circumference (for example, the length of the cloth material comprising the lateral edges of certain models of a 3M® N95 face mask shown in prior art FIGS. 3 and 4, 3M® being a registered trademark of the 3M Corporation). A medical grade silicone is selected according to a Shore hardness scale to be deformable but tight enough so as to fit permanently around the lateral edges of most face masks such as a Shore A hardness scale between 10 and 40, preferably approximately 25. An outer shell may contain the medical soft gel material and when coated on the face side with a petroleum jelly or Shore A 0 gel or jelly will wet or protect any exterior cloth lateral edges from air gaps. The coating of the face side of the U-shaped channel member with a soft medical silicone gel or petroleum jelly serves at least three purposes. A first purpose is to wet or render leak-proof a lateral edge, for example, comprising cloth or plastic to prevent leakage of airborne pathogens to or from the facial area. Ideally, a face mask should not be moved once applied to the face. The movement may alleviate discomfort but cause leakage of airborne pathogens to the face. A second purpose is comfort. When a U-channel, circular or clasping soft cushion covering clasps a face mask's lateral edges, any discomfort brought on by use of elastic straps or string ties with movement of the face and head may be alleviated. A third purpose is to use a source of ultraviolet light at frequencies between 200 and 230 nanometers, especially 207 to 222 nM, which may have controls and displays mounted on the cushion or replacing any filter body in face mask for particles, for example, a filter of an N95 mask. A feature of the present cushion is its ability to work with a breathing cartridge that may replace a particle filter on a mask by providing an ultraviolet light source that is not damaging to the skin for deactivating any coronavirus located, for example, in the interior chamber of an N95 mask. A circuit comprising an on/off switch, a USB port for charging a battery for powering the ultraviolet light source, a battery indicator, a Bluetooth indicator and the like may be located on the U-shaped channel or comprise a component of the ultraviolet light source, for example, replacing a particle filter of the face mask Special provisions may be used in the nasal area to provide a protection of nasal exhalations from rising upward toward the eyes of the wearer, especially to prevent fogging of eyeglasses. While foam rubber is known used in N95 masks and a nose plate is known from the prior art oxygen and ventilator masks of FIGS. 1 and 2, these can be uncomfortable and replaced by deformable nose bridges coated with petroleum jelly or medical 0 hardness silicone gel. The coating also should also prevent the wearer from suffering any long-term adverse reactions to the coating and be medically safe.

These and other features of the present invention will be made clear from the Brief Description of the Drawings which follows along with the Detailed Description which follows the brief description.

BRIEF DESCRIPTION OF THE DRAWINGS

A convention is used with the drawings of the present invention such that the first number of a reference numeral such as the 1 in 125 represents the figure number of the item where a particular component 1XX first appears where XX (25) is intended to comprise a similar component in a later discussed figure.

FIG. 10A shows a typical face mask 1000 in front view which may be any of an oxygen mask, a ventilator mask, a disposable face mask or a surgical mask 1000 having a cushion manually fitted around and clasping lateral edges of the mask 1050 (FIG. 10B). A soft U-shaped medical silicone channel cushion 1075 is seen in cut view 10B-10B for clasping the lateral edges 1050 of the mask 1030 is continuous and is manually fitted to the lateral edges 1050 of the mask 1030 having straps 1040.

FIG. 10B shows FIG. 10A in cross-section at a lateral edge of the mask 1050 such that the soft U-shaped medical silicone section 1030 clasps the mask at lateral edge 1050. Aperture 1005 filled with air under pressure may assist in clasping mask edges 1050

Now a detailed description of FIGS. 1-14 will be provided having briefly described the present invention.

DETAILED DESCRIPTION

Figure 3:
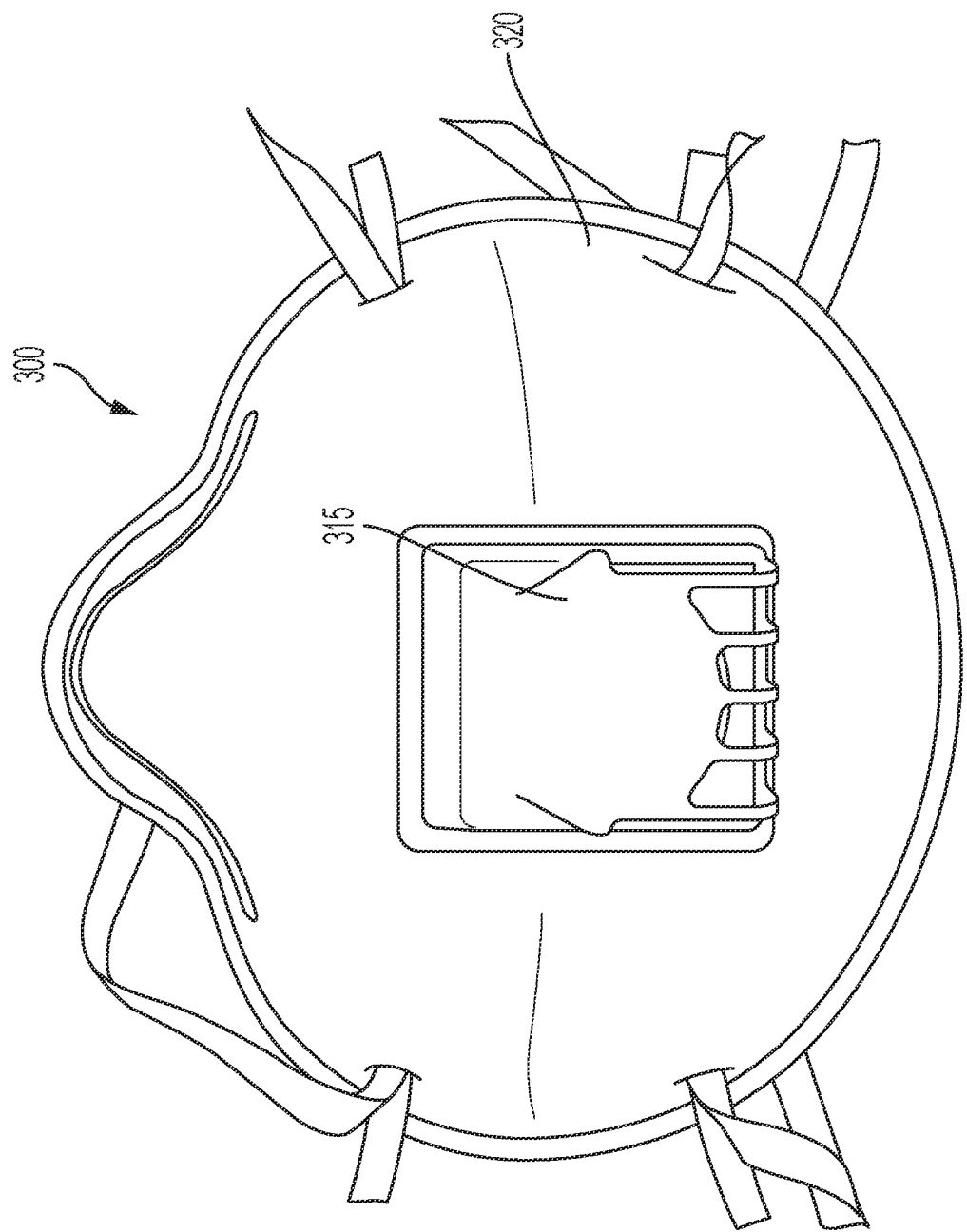
FIG. 3 shows a front view 300 of a 3M® N95 rated face mask. Of importance is the circumference of the face mask comprising a flexible border cloth or hardened paper material (lateral edge 320) which may allow leakage of inhaled/exhaled air from the mouth and nose and fails to form a tight seal against leakage of viral pathogens to the exterior.). A nose grid 315 comprises a particle filter for the N95 mask, and the face mask is especially recommended for healthcare workers.
Figure 4:
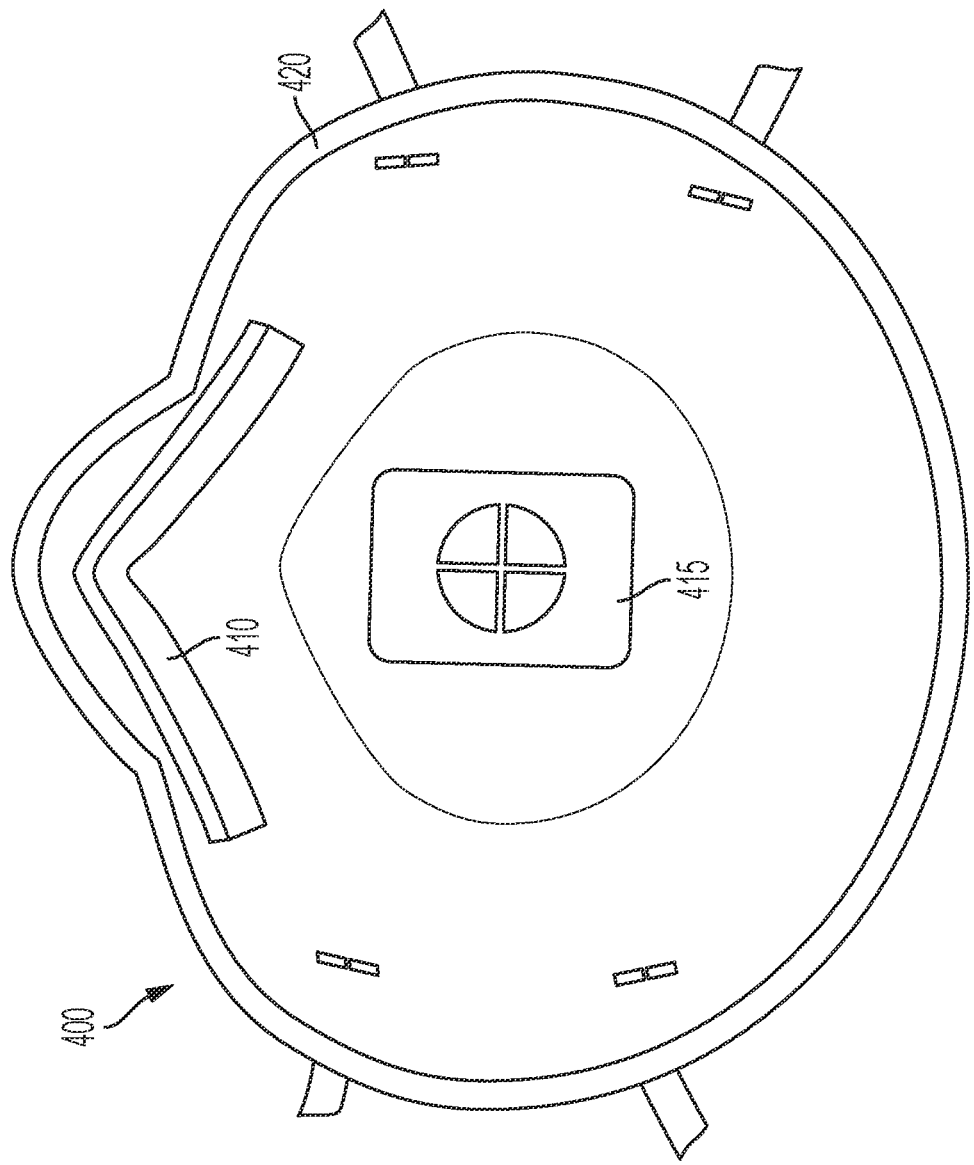
FIG. 4 shows a rear view 400 of the 3M® N95 rated face mask example face mask 300 of FIG. 3. Notice that there is a grid 415 (the opposite side of grid/filter 315 of FIG. 3 or a different particle filter) for receiving air from the exterior, filtering the inhaled/exhaled air from/to the exterior of the face mask. In addition, a foam rubber nose bridge 410 may be formed to help prevent exhaled air from rising above the nose to the eyes of the wearer. The foam nose bridge 410 may or may not effectively prevent a wearer of the face mask who wears eyeglasses from having their glasses fog. Grid 415 may be replaced according to an embodiment of the invention by an ultraviolet (UV) source and accompanying circuitry for powering the UV source or the power circuitry may comprise a reachable portion of the U-shaped channel cushion for protecting a user's face.

The present invention is directed to a cushion for a face mask, face and nose protector that may further include an ultraviolet light source replacing a typical particle filter with the ultraviolet source for deactivating virus pathogens. The cushion 1400 provides greater comfort to the wearer and prevents leakage of exhaled air (that may contain coronavirus) from the lateral edges of the face mask which will be described with reference to FIGS. 1-14. A convention used throughout relates to the reference numerals which may be used in each figure of the format XXYY where XX is the figure number and YY is a component reference number. Referring briefly, for example, to FIGS. 3 and 4, with respect to filter 315 and filter 415, 4 represents the figure number and 15 represents the component such as a particle filter.

Figure 1:
FIG. 1 shows an example of a prior art oxygen face mask 100 having a lateral edge 125 that appears to comprise plastic that can be elastically tied to the face. The pressure caused by the elastic or material ties around the head may cause discomfort in the regions of the face protected by lateral edges 125. The oxygen face mask 100, being solid, may not fit the wearer such that oxygen (viral pathogen) leakage may not be avoided.

FIG. 1 shows an example of a prior art oxygen face mask 100 having a lateral edge 125 that appears to comprise plastic. The face mask 100 with its surrounding lateral edge 125 can be elastically tied to the face (around the head shown). The pressure caused by the elastic or material ties around the head may cause discomfort. The oxygen face mask 100 being solid, may not fit the wearer so that the mask is uncomfortable to wear and such that oxygen leakage from the lateral edges 125 should be avoided. Notice also that there appears to be a nose bridge for preventing a loss of oxygen in the direction of the eyes. As will be discussed herein with reference to FIGS. 6-10B, a soft cushion shell of the present cushion invention may provide a soft gel or pressurized air internal to the soft cushion shell that is intended to help clasp lateral edges, relieve discomfort and prevent exhaled air from escaping from lateral edges of, for example, the face mask 100 comprising an oxygen mask.

If this patient were to wear this mask 100, as is, all day long and night, with apparently plastic edges, it is highly likely that the patient will have discomfort. The wearer may develop skin conditions form wearing the mask for long intervals, perhaps abrasions or even contusions. It is a feature of the present invention to provide a soft cushion shell that fits over and clasps the mask edge and protects the wearer's face, adapted to be used with a coating for contacting the mask to the face and a coating for contacting the lateral edges of the mask underneath the shell to protect from leakage of oxygen to the outside air and promote comfort.

Figure 2:
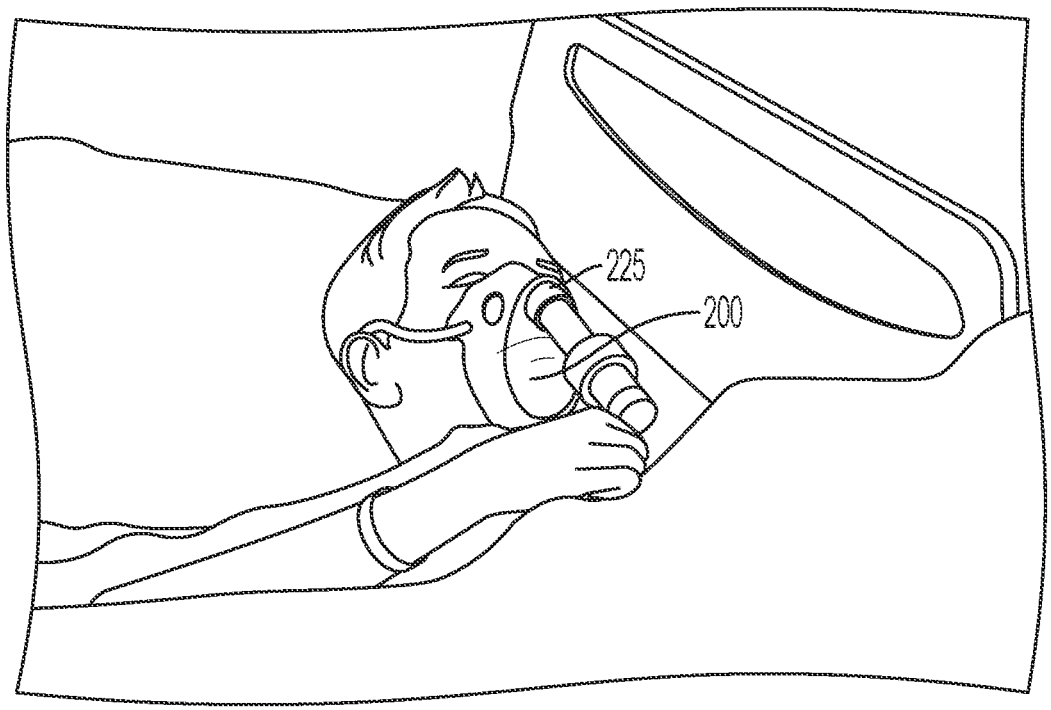
FIG. 2 shows a prior art ventilator face mask 200 which may comprise a solid plastic lateral edge 225 that may rub against the skin and irritate the facial regions where the lateral edges 225 are pulled tight or even cause some forms of disease. The purpose of the ventilator is to deliver and potentially force air into the lungs for a person having difficulty breathing. Adjustable elastic straps may hold the mask to one's face, but the patient may be forced to rest in one position in order to safely and comfortably wear this ventilator mask.

FIG. 2 shows a prior art ventilator face mask 200 which may also comprise a solid plastic edge 225 that may rub against the skin and irritate the skin. The purpose of the ventilator is to deliver and potentially force air into the lungs for a person having difficulty breathing. Adjustable elastic straps may hold the mask to one's face. The pressure caused by the elastic or cloth material ties around the head may cause discomfort where the lateral edges 225 of the mask contact the face. The ventilator face mask 200 being made of a solid material such as plastic, may not fit the wearer such that pathogen leakage can be avoided. A filter for filtering inhaled oxygen or exhaled air may be fitted with a cartridge for virus inactivating ultraviolet light. A soft cushion shell may be provided as will be discussed with reference to FIGS. 6-10B, 11A-14 comprising a medical silicone shell component that contains a soft gel or jelly that is intended to relieve discomfort and prevent air from escaping from lateral edges of, for example, a face mask comprising an oxygen or ventilator mask. Also, the shell cushion (not shown) may be coated with a soft gel or petroleum jelly that alleviates a patient's facial discomfort.

In other words, the ventilator mask shown, appears to be very similar to the oxygen mask of FIG. 1. The patient appears to exhibit some swelling in his face around the mask 200, perhaps caused by plastic lateral edges which can be avoided by using a soft cushion tubing like structure with soft gel or petroleum jelly coating that can protect the face and prevent oxygen leakage.

FIG. 3 shows a front view 300 of a prior art 3M® N95 rated face mask. Of importance is the circumference of the face mask comprising a flexible border soft cloth material which may allow leakage of air intended to be inhaled by the mouth or nose. The lateral edges 320 form a circumference that fails to form a tight seal against leakage of viral pathogens to the exterior. A particle filter grid 315 and cloth/hardened paper material 320 is shown. The particle filter 315 is intended for removing particulate matter from air or oxygen inhalation and exhalation. As will be discussed further herein, an ultraviolet (UN) light source/filter or cartridge may replace the standard filter grid 315 and be operated from a circuit accessible to the user located on a cushion or comprise a circuit of the U/V light source cartridge. The material forming the mask may be multi-layers so that 95% of small viral pathogens on the order of three microns cannot enter the mask and reach the patient. Furthermore, the UVC light source will inactivate coronavirus that may be inhaled or exhaled without U/V damage or burn to one's skin.

The N95 face mask is most popular for use by healthcare workers in hospitals and wards when they are working closely with diseased patients. The cloth or composite paper material lateral edges may be adapted to receive a soft cushion apparatus according to the present invention that is elastic and of sufficient circumference to reach around the entire mask clasping the edges of the N95 mask. As with FIGS. 1, 2, and 3, please refer to FIGS. 6-14 for an explanation of the present invention.

FIG. 4 shows a rear view 400 of a 3M® N95 rated example face mask 300 of FIG. 3. Notice that there is a grid 415 (which may be the reverse side of grid/filter 315) for receiving air from the exterior, filtering the inhaled air of particles and emitting filtered breathed air to the exterior. In addition, a foam rubber nose bridge 410 may be formed to prevent breathed air from rising above the nose to the eyes of the wearer. The foam rubber nose bridge 410 may or may not effectively prevent a wearer of the face mask who wears eyeglasses from having their glasses fog. A purpose of the cushion of the present invention (not shown) is 1) to protect the skin of the wearer and 2) comprise circuits/buttons for operating a replacement U/V filter 415 replacing filter 415 for deactivating viral pathogens within an interior chamber of the N95 mask.

According to the present invention as described by FIGS. 6-14, the lateral edges 420 are sealed by a detachable and reusable clasping elastic shell cushion that fits and clasps the entire circumference of the lateral edge 420. Also, the foam rubber bridge 410, if detrimental to the patient, may be fitted with a nose bridge constructed similarly to the protective and wetting shell soft cushion, for example, of medical silicone gel.

Figure 5A:
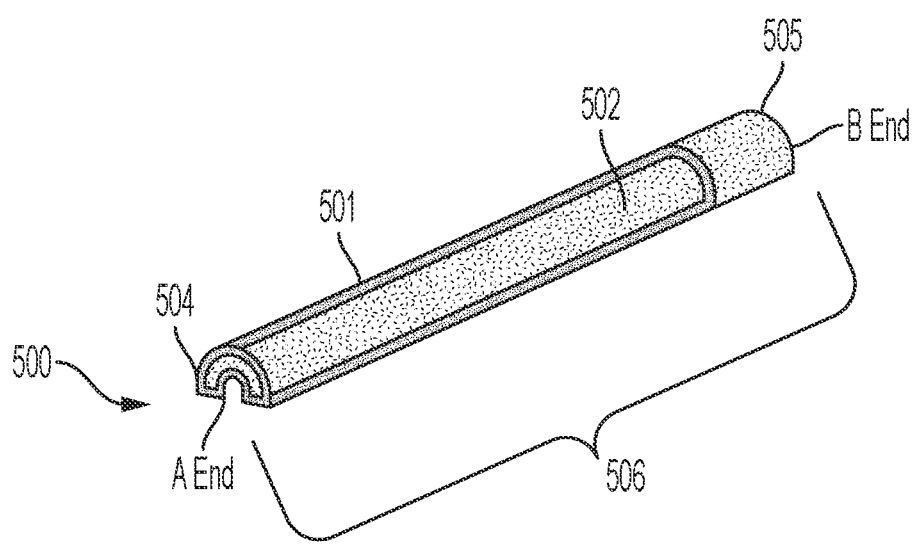
FIG. 5A shows a cross-section 500 of a U-shaped channel or semi-circular shaped exterior shell of cushion apparatus for surrounding and clasping the lateral edges of a face mask, for example, face masks 100, 200, 300 and 400 of prior art FIGS. 1, 2, 3 and 4. In one embodiment, the exterior shell 501 has a semi-circular or U-shaped channel cross-section which will be discussed with respect to prototype FIGS. 10B through 12B. Other useful shapes are a clam or clasping shape (like a clam shell). Inside the exterior shell 501, the shell preferably contains a soft gel, jelly or petroleum jelly 502 or air under pressure which helps to make the cushion lighter. The U-shaped channel is stretchable and flexible and, in combination with the outer shell 501, may be used to clasp the lateral edges of, for example, the entire circumference of the lateral edges of an N95 face mask. Reference numerals 504, 505 are A and B ends intended to show insertion of soft silicone medical grade gel or air under pressure into shell 501. Reference numeral 506 may represent the circumference of lateral edges of a face mask such that the cross-section 504 or 506 may be tapered, molded together, plugged or clasped together and claps a cloth or hardened paper material such as the lateral edges of an N95 cloth mask. As will be discussed with reference to FIG. 10B, 11B or 12B, a continuous circle of cross-section 504 may be manipulated by the user to 1) coat the face side with petroleum jelly or soft silicone gel so as to wet the N95 cloth lateral edges and 2) prevent air leakage to the eyes or outside the face mask.

FIG. 5A shows a cross-section 500 of a U-shaped channel or exterior shell of cushion apparatus (see FIG. 9) for surrounding the lateral edges of a face mask, for example, N95 face masks 300 and 400 of FIGS. 3 and 4. In one embodiment, the exterior shell has a semi-circular or U-shaped channel cross-section which will be discussed with respect to prototype FIGS. 10A and 10B and FIGS. 11A through 14. Inside the exterior shell coating 501, for example, of Shore A extra soft hardness 10-40 (see FIG. 5B for a Shore A hardness scale), the shell preferably contains a soft gel or air under pressure 502 which is flexible and in combination with the shell 501 is used to clasp the lateral edges of, for example, the entire circumference of an N95 face mask, oxygen mask or ventilator mask (or surgical mask and shield combination, not shown). See FIGS. 10A and 10B. Reference numeral 504, an A end, for fitting to a B end 505 is intended to indicate ends of a shell 501 that are formed to meet one another during injection molding in one embodiment that is made just for one common mask model, not necessarily an N95 mask that may have a varying circumference from another N95 mask model. A plurality of buttons and displays for operating an ultraviolet source replacing a known N95 filter may be located within reach of the user on a cushion or on an ultraviolet cartridge of the present invention. The buttons/displays may comprise on/off, Bluetooth indicator, a battery level indicator and a port such as a USB port for providing charging power to the battery. In another mode of manufacture, by using a plug, by tapering one end to fit into the other or other means, a measured length of U-channel may be fitted to fit the lateral edge of any face mask. For example, an A end may fit into a pocket formed in the B end to receive the A end such that a typical circumference of a lateral edge of a face mask may be covered by the shell clasping the lateral edges having been hand-fitted around the mask to match its circumference. See FIGS. 10A and 10B and FIGS. 11A-14 for variations with an ultraviolet light source for deactivating viral pathogens as it emits selected ultraviolet wavelengths but does not damage facial skin or eyes because of the choice of U/V wavelength/frequency.

One of many known injection molding processes may be used for forming a complete unit for fitting a given mask or for making a self-installable sized mask that may have A and B ends (FIG. 5A) for plugging into one another. During injection molding processes, alternatively. the cushion around a face mask may be manufactured as a complete circumference designed to fit a particular mask such as an N95 mask having specific model numbers with a predetermined circumference of lateral edging. Per FIG. 5A, when injection molding is used to process the soft gel/pressurized air part 502 of the cushion, the gel/pressurized air part 502 may be injected into the cushion length (circumference) 506. An air pocket may be formed at the U junction (upper side) under pressure to assure that the two prongs of the U will clasp a specific make and model of face mask. Alternatively, the A end 504 of U-channel, semi-circular cushion having length 506 may be tapered to fit in the B-end 505. Outside air cannot enter the U-shaped channel which is sealed. Component 502 may be an extra soft gel or jelly material of a Shore A hardness of extra soft or in the range of 0 to 10 if comprised of medical silicone quality gel. As will be further described herein, the internal material 502 may be air or hydrogen under pressure. Reference numeral 505 is intended to show the insertion of soft gel 502 within the shell 501 for clasping the lateral edge of a given make and model of face mask. Length 506 is intended to be the typical circumference of a given make and model or models of face mask. From measuring the circumference of various types of face masks, it has been determined that most face masks have the same or similar overall circumference. In other words, one size soft cushion 506 of predetermined circumference will fit many makes and models of face masks.

Figure 5B:
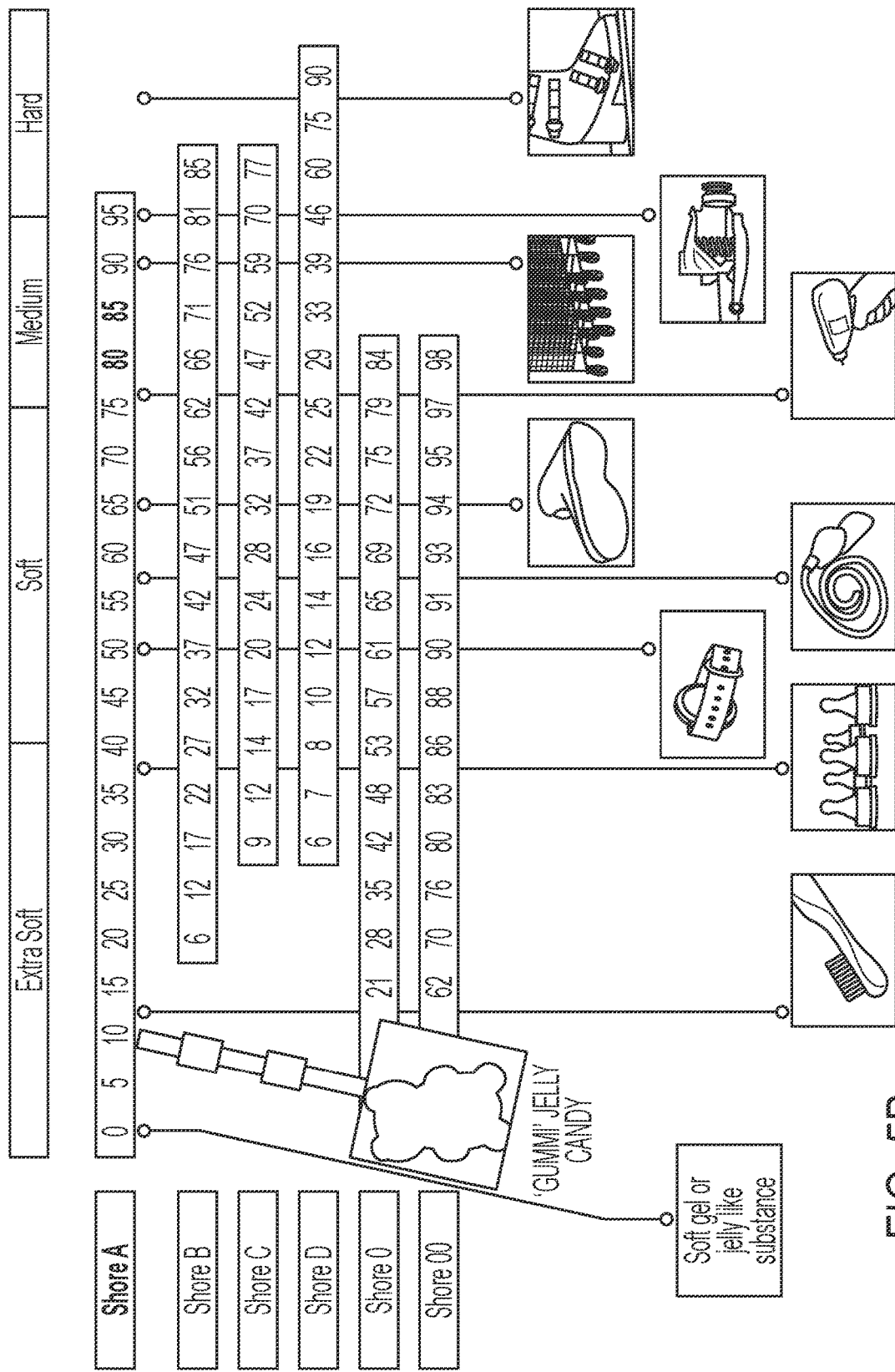
FIG. 5B is an expanded view of a Shore A—00 hardness scale and examples of uses of silicone for a substance such as a soft gel or jelly-like substance that may be used as a coating or a filler from "extra soft" to "hard". Silicone in the lower hardness numbers such as 00-40 may have elastic qualities allowing the silicone to be stretched and manually coated inside and out to protect the face and to grasp the lateral edges of the face mask.

FIG. 5B shows a Shore hardness scale used by manufacturers of medical silicone gel to qualify the hardness of silicone material. The Shore hardness is intended to be between 00A and 40A (extra soft) of a durometer scale for both soft gel or a jelly like substance interior and a hardness between a range of 10-80 on the extra soft to medium hard Shore A Hardness scale for the exterior shell-like clasping component 501. Preferably, the shell 501 will have a greater Shore hardness that is harder than the soft gel/air interior or coating 502 so that is elastic and formable as it covers the lateral edges of a face mask of many types and is detachable and reusable from a PPE face mask.

Figure 6:
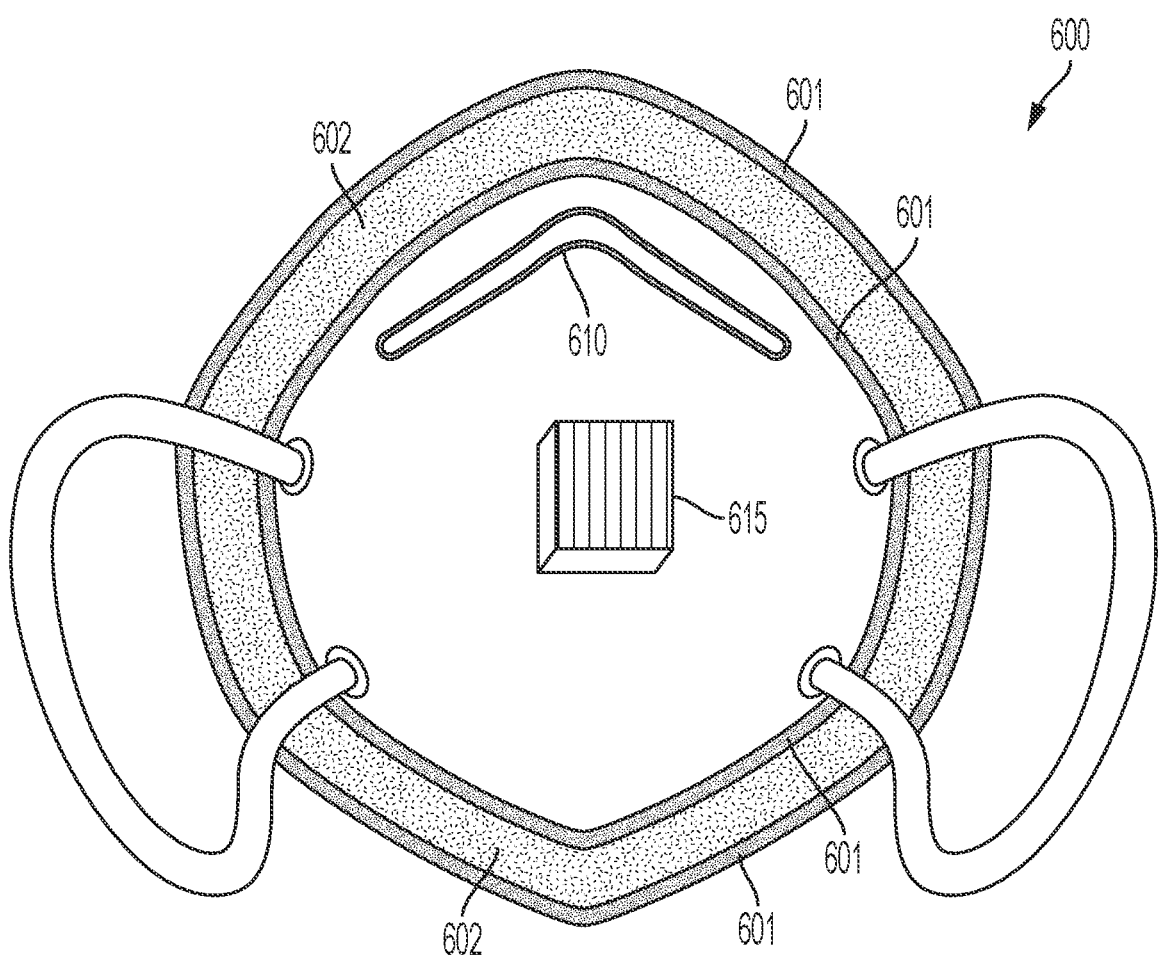
FIG. 6 shows another detailed cross-section example of a typical interior of an N95 face mask 600 fitted with a U-shaped channel or semi-circular shaped shaped shell 601 (shown in cross-section) which clasps cloth/hardened paper lateral edge material of the N95 mask (lateral edges not shown); (see, for example, lateral edges 420, FIG. 4). Interior soft gel or air under pressure 602 serves to moistens the fabric or cloth of lateral edges of the N95 mask and face side or interior soft gel or petroleum jelly wets the cloth material lateral edges and prevents air leakage. Exterior soft gel or petroleum jelly coating the face side shell 601 promotes a comfortable and snug fit to the face. Nose bridge 610 is shown as in FIG. 4 comprising foam rubber but may be coated with petroleum jelly or soft gel 602.

FIG. 6 shows a detailed cross-section example of a typical interior of an N95 face mask 600 fitted with a U-shaped channel or semi-circular shaped cushion shell 601 of the present invention which is elastic, detachable and reusable, and may clasp cloth or plastic or other lateral edge material (not shown in this figure). Interior soft gel or air under pressure 602 may be used as the interior of a cushion (see FIG. 5A). Petroleum jelly or soft gel may be used on the exterior face side or inside of cushion 601 to moisten fabric of lateral edges or protect the face, prevent exhaled air leakage and promote a comfortable fit to the face. Interior gel 602 may alternatively comprise air, light gas such as hydrogen or other medically safe liquid or gas under pressure to assure clasping of the N95 mask by make or model. Nose bridge 610 is shown as in FIG. 4 comprising foam rubber that may be clasped by, for example, a U-shaped cross-section 601, 602 lengthwise portion of cushion and coated on its exterior with soft gel or petroleum jelly (or other medically safe lubricant) to seal the nose bridge and be expected to be more comfortable and tighter fitting than an N95 foam rubber nose bridge. Filter 615 may be replaced by a cartridge containing ultraviolet light for deactivating COVID 19; (see FIG. 13).

Figure 7:
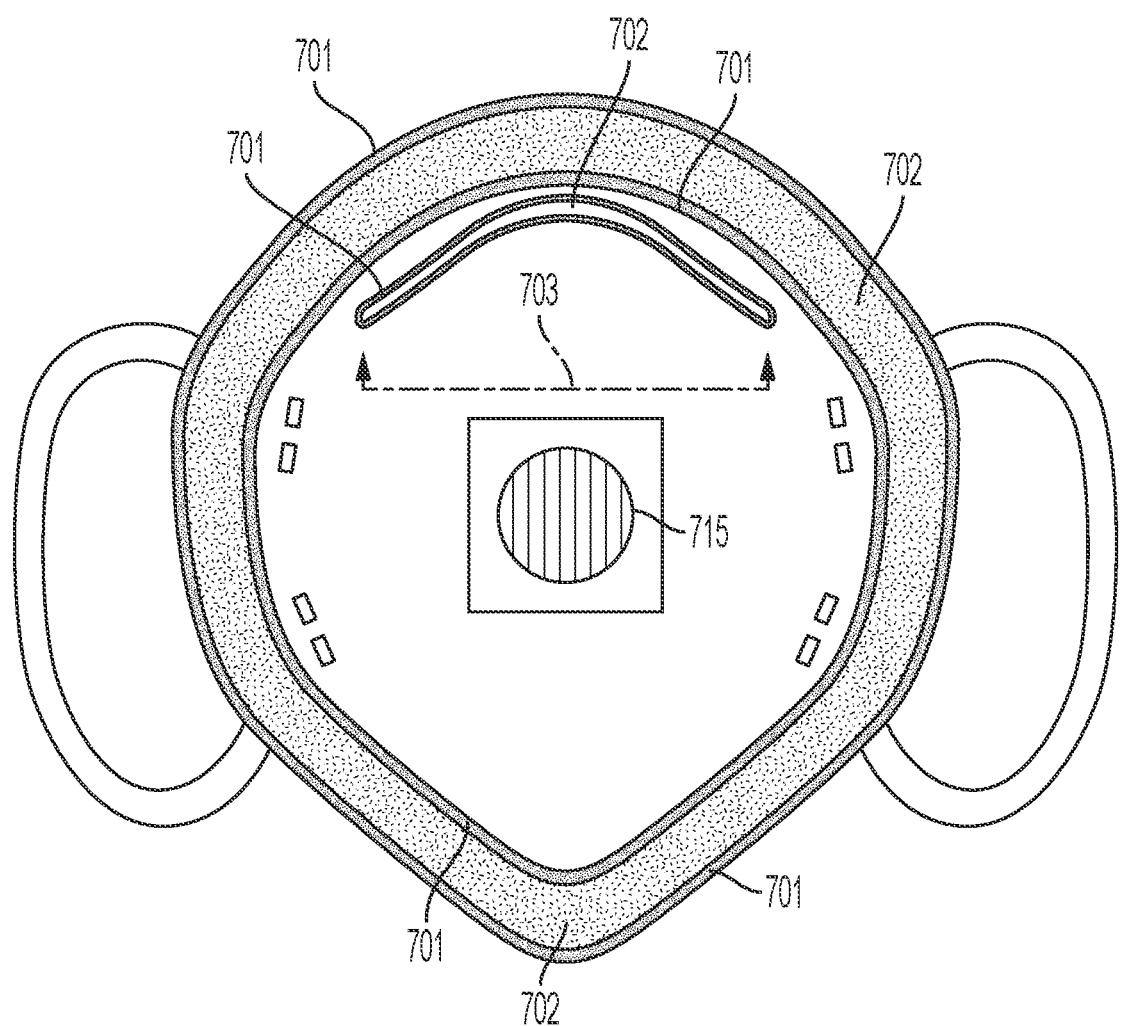
FIG. 7 provides further interior details of the present invention than FIG. 6 and shows a foam nose bridge of foam 410 of FIG. 4 adapted to be clasped by a nose bridge 701, 702 comprising shell silicone gel 701 and silicone gel or air 702 for better preventing the nose bridge 410 from leaking air to the mask exterior. Reference numeral 703 indicates that a soft silicone edge cushion may replace prior art foam rubber when clasping the foam rubber as a nose bridge on the top of a wearer's nose (for example, a clasping shell 701 that clasps the existent foam rubber for comfort and to protect against air leakage to the eyes on exhalation).

FIG. 7 shows another example of an N95 face mask and provides further details of the present invention than FIG. 6, particularly regarding a nose bridge having an average length 703. FIG. 7 shows a foam rubber nose bridge of foam 410 of FIG. 4 covered by and adapted to be clasped by a nose bridge cushion 701, 702 comprising a length of shell silicone gel 701 and containing silicone gel or pressurized air 702. The nose bridge 701, 702 need not be elastic, but may be of silicone and flexible to better fit a nose, as it is assumed to be of the same length as foam rubber bridge 410 of FIG. 4. The additional nose bridge 701, 702 of triangular length 703 may be coated with soft medical grade soft gel or petroleum jelly to seal the nose bridge and protect the wearer's nose from damage from rubbing foam rubber. Grid/filter 715 (replaceable by a UVC cartridge per FIG. 13) is shown and ear loops are shown for holding the N95 mask to the ears of a wearer.

Figure 8:
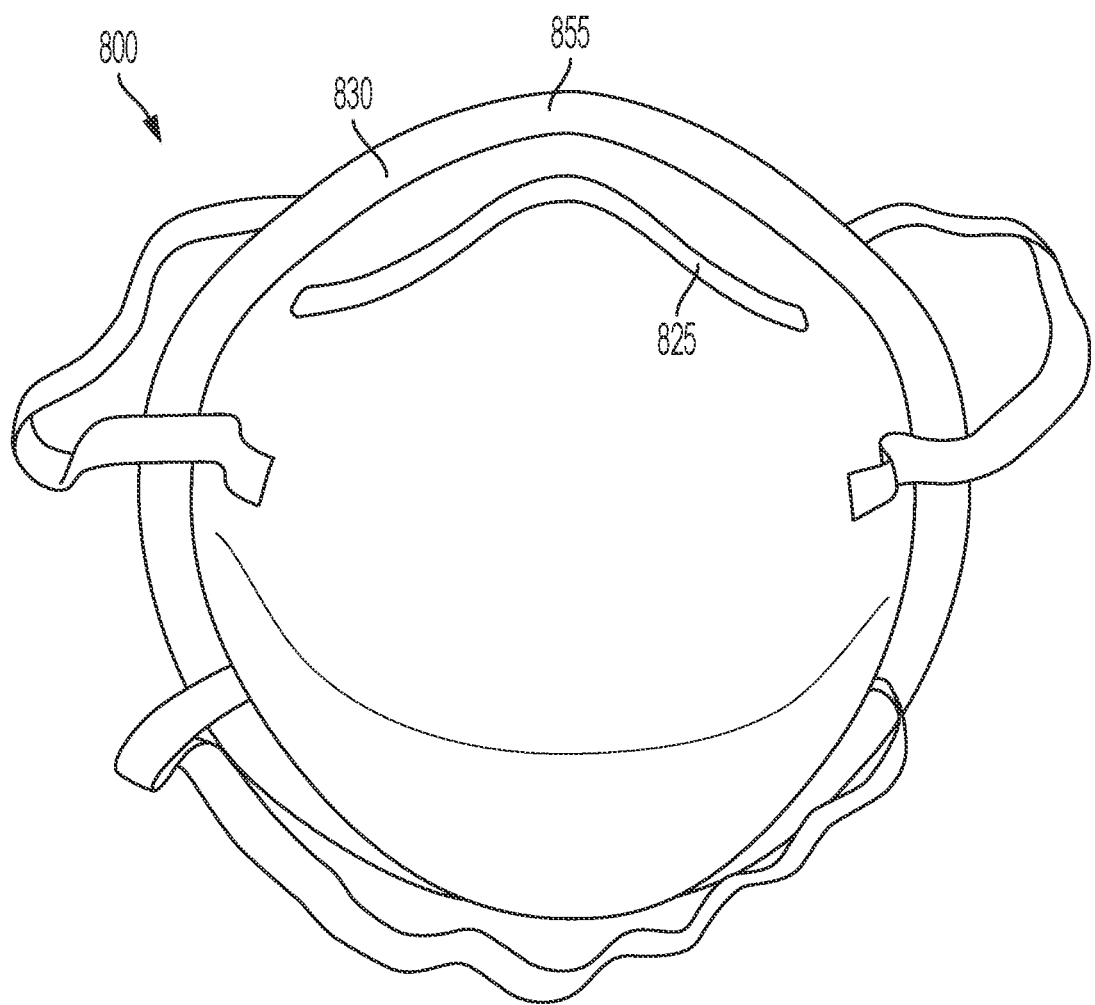
FIG. 8 provides the interior details 800 of an N95 face mask utilizing the present invention. The mouth and nose grid 415 of FIG. 4 has been removed. A U-shaped, semi-circular or mostly circular exterior shell 830 has been carefully fitted around the lateral edges 855 (underneath shell 830) of the face mask 800 such that the lateral edges 855 have been fitted into the shell and coating 830. Note that the shell 830 is continuous, of predetermined length, and elastic and so can fit around the N95 mask lateral edges and help shape the N95 mask. Also, the foam rubber nose bridge has been replaced with a nose bridge 825 which is deformable and can conform to the bridge of the nose of a wearer by lightly pressing on the deformable nose bridge 825 squeezing any foam rubber underneath. The nose bridge 825 may protect the nose by a wearer applying a medical silicone gel or petroleum jelly (not shown) to the surface of the bridge 825 before pinching it on the foam rubber nose bridge and adjusting its form.

FIG. 8 provides the interior details of an N95 face mask prototype 800 utilizing the present invention, cushion 855 covering lateral edge 830 underneath. The mouth and nose grid filter 415 has been removed. Elastic bands (which may be uncomfortable) are shown for the ears or to fit around the neck or back of the head (not shown). A detachable or reusable U-shaped channel or exterior shell cushion 855 has been carefully fitted (because it is elastic and of similar circumference) around and clasps the lateral edges 830 (underneath) of the face mask cushion 855. Also, the foam rubber nose bridge of the N95, in this embodiment, may been replaced with a nose bridge 825 which is deformable such as soft silicone similar to 830,855) and can conform to the bridge of the nose of a wearer by lightly pressing on the deformable nose bridge 825 to deform it to the shape of the wearers nose. The nose bridge 825 may protect the nose by applying a medical silicone gel (not shown) or jelly to the surface of the bridge 825 before placing it on the nose and adjusting its form. Also, the nose bridge 825 may be adapted to clasp the foam rubber nose bridge equipped with the N95 mask interior (see FIGS. 6 and 7) but adapted in size for the individual wearer (who may have a larger/smaller nose than most wearers).

Per FIG. 8, a wearer may self-install a cushion of FIG. 5 around the lateral edges of a given face mask that has a lateral edge of a different circumference than a well-known mask such as the N95. A lengthy piece of U-channel tubing having A and B ends per FIG. 5 may use a juncture point of a length of U-shape channel such as a plug (not shown) to plug one end to the other having cut the cushion length of FIG. 5 to fit the face mask. One of the A end or B end of 830 lateral edge or cushion 855 may be tapered to fit into each other. A wearer would have to cut the cushion to fit cutting the end that is not tapered or for using a plug or other device to join the cut ends of the cushion. The cushion 855 may be cut to fit any circumference and a plug may be used to close the cushion 855 to clasp the lateral edges 830 (underneath 855) of the face mask.

Also, per FIGS. 5, 6, 7 and 8, the cushion of the invention may have gel inserted or no gel inserted. Air, hydrogen or other light-weight substance may be introduced under pressure before sealing with a plug (preferably used because it reduces weight of the cushion). Air under pressure may be used in place of, for example, soft gel filler 502 or harder shell substance 501 and may be used under pressure to close the cushion U-channel and clasp the cloth or plastic lateral edges of a mask. Referring, for example, to FIGS. 10A and 10B, preferably air (or alternatively) hydrogen or soft gel of light weight may be used under pressure as the filler of the U-channel opening 1005 (FIG. 10B) and help clasp lateral edges 1050 of PPE. Air is preferable for reducing weight of the cushion, but the cushion must be flexible to surround and clasp lateral edges of an associated face mask.

Figure 9:
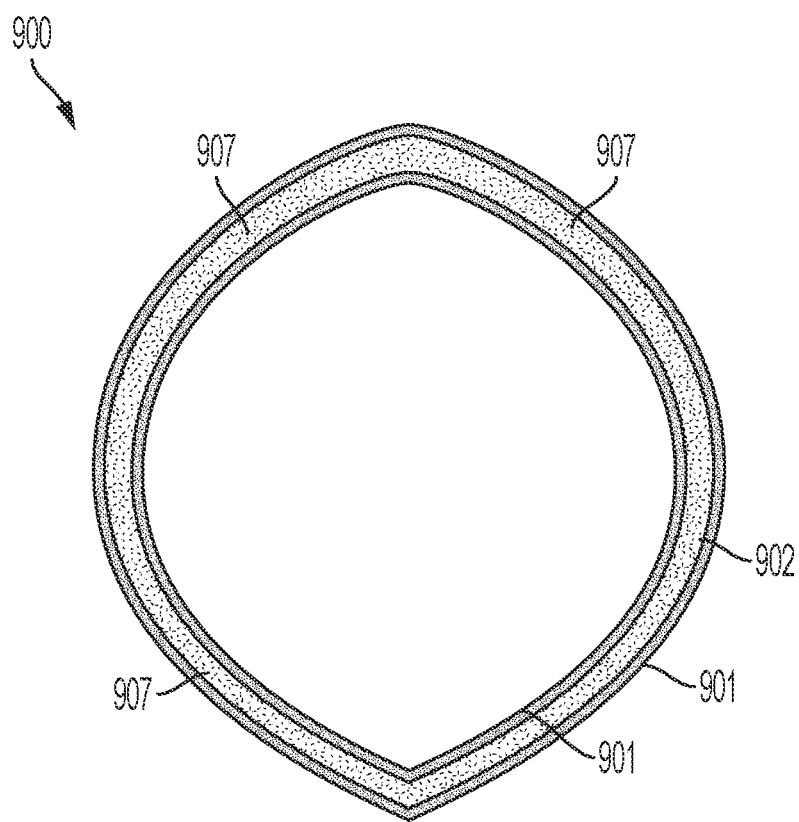
FIG. 9 shows a formed cushion for a face mask having the same or a similar circumference as the lateral edges of an N95 face mask of FIGS. 3 and 4. Component 901 is the clasping shell which clasps the lateral edges of a face mask and component 902 is the interior of the U-shaped channel which may coat cloth/hardened paper/plastic material of a lateral edge of a face mask and prevent air from escaping from the face side of the face mask. Reference numeral 907 is intended to represent that the shell 901 and interior coating 902 are continuous and form a predetermined circumference that is elastic medical silicone for protecting the wearer's face and having a coating for preventing against leakage.

FIG. 9 shows a formed soft cushion 900 of the present invention in a circumferential or somewhat circular shape for fitting to a face mask of predetermined circumference having the same or a similar circumference as the lateral edges of, for example, an N95 face mask of FIGS. 3 and 4 or other make and model of mask. Component 901 is a clasping shell which clasps the lateral edges of a face mask, 907 is a filler and the cushion 900 is detachable from one face mask and reusable on another. A face mask equipped with a cushion 900 preferably covers the mouth and nose of a wearer. Cushion 900, shell 901 may be used to make the shell more formable and may be coated with petroleum jelly or soft gel on a face side to prevent air from escaping from the sides of the face mask and make the mask more comfortable to wear. Component reference numeral 907 is intended to point to a clasped lateral edge of, for example, an N95 or other make and model of face mask.

FIG. 10A and FIG. 10B are intended to be considered together where FIG. 10A is a front view of a face mask 1000, and FIG. 10B is a cross-section taken of an alternative U-shaped cushion 1075 of FIG. 10A. The face mask 1000 of FIG. 10A has a circumferential embodiment of a soft U-shaped medical silicone tube-like cushion 1075 for clasping the lateral edges of any face mask 1030 of similar circumference with straps 1040. The paper, cloth or plastic mask body 1030 may be manipulated by hand so U-shaped channel 1030 (FIG. 10B) and gel or air under pressure 1005 may clasp the lateral edges 1050 (FIG. 10B) of a face mask 1000 and have a air under pressure aperture 1005 (FIG. 10B) as discussed above. Its exterior may be coated or the lateral edges of the face mask 1000 may be wetted with extra soft silicone hardness 0 to 10, petroleum jelly or other soft jelly-like substance to prevent air from leaking from the mask where U-shaped shell 1030 (FIG. 10B) clasps a face mask 100 lateral edge 1050 (FIG. 10B) or on the face side of the cushion 1030. Gel or jelly like substance, air under pressure or other lightweight material under pressure 1005 may be seen interior to clasping U-shaped shell 1030 so channel 1030 may be reusable and attachable or detachable from lateral mask edges. FIG. 10B portions 1030, 1005 comprise a cross-section 1075 (FIG. 10A) of a cushion embodiment having lateral edges 1050. FIG. 10B comprises a clasping shell 1030 for clasping a lateral edge 1050 of a face mask. The light-weight air or hydrogen 1005 under pressure may be used in an aperture of the cross-section to cause the U-channel of the shell 1030 to clasp the lateral edges 1050 of a face mask.

A method of manufacture of a soft shell cushion apparatus as shown in FIGS. 10A and 10B may comprise injection molding. The apparatus hole 1030 containing a material (preferably air or hydrogen under pressure) in the length of tubing shown as cross-section 1050 may form a self-installable fit to a face mask comprising the following steps of manufacture. One first forms a U-shaped channel of predetermined length of medical grade silicone having an extra soft Shore A Hardness scale value between 10 and 80, the predetermined length being measured by measuring a circumference of lateral edges of, for example, an N95 face mask. Then, the U-shaped channel may have an aperture 1005 along its length filled with air or hydrogen under pressure, the gas under pressure completely filling the length of the U-shaped channel cushion and causing U-channel 1030 to clasp lateral edge 1050 of face mask 1000. A final step is using injection molding processes to manufacture a cushion filled with air under pressure for fitting a particular mask of predetermined lateral edge circumference. In an alternative method, the A and B ends of a shell 1030 may be tapered or fitted together with a plug for sealing A and B ends of the U-shaped channel and air under pressure aperture 1005 by joining one end to the other after the filling step. Use of one of heat and bonding material may alternatively be applied to the A and B ends (if the shell 1030 is not made in one piece) to join the ends together to comprise a sealed loop. FIGS. 11 through 14 will discuss the implementation of an ultraviolet light source for filtering and deactivating viral pathogens so that any escaping inhaled/exhaled breath does not contain pathogens.

Other variations of the embodiment of FIG. 10A or 10B may come to mind by careful consideration of the depicted embodiments. Improvements to shape and elasticity may come to mind of one of ordinary skill to fit the cushion apparatus to, for example, the plastic edges of an oxygen or ventilator mask, to a surgical mask, to a hood or to an N95 face mask and face shield to improve comfort and safety and prevent escape of air or oxygen above the nose.

Coronavirus disease 2019 (COVID-19) was first reported in December 2019 and then characterized as a pandemic by the World Health Organization on Mar. 11, 2020. Despite extensive efforts to contain the spread of the disease, it has spread worldwide with over 95.1 million confirmed cases and over 2.3 million confirmed deaths as of Jan. 18, 2021. [1] Unfortunately, there are over 24 million confirmed cases and over 398 thousand confirmed deaths in USA as of Jan. 18, 2021. [2] The severity of the 2020 COVID-19 pandemic warrants the rapid development and deployment of effective counter measures to reduce person-to-person transmission such as wearing effective face masks and developing vaccines.

Transmission of severe acute respiratory syndrome (SARS), the beta coronavirus causing COVID-19, is believed to be contracted both through direct contact and airborne routes (mouth and nose), and studies of SARS-COVID-19 stability have shown viability in aerosols for at least 3 hours. [3] Given the rapid spread of the disease, including through asymptomatic carriers, [3] it is of clear importance to explore practical mitigation technologies that can inactivate the airborne virus before inhalation/exhalation of air and thus limit airborne transmission.

Germicidal UV (GUV)—refers to short-wavelength ultraviolet "light" (radiant energy) that has been shown to kill bacteria and spores and to inactivate viruses. Wavelengths in the photobiological ultraviolet spectral band known as the "UVC," from 200 to 280 nanometers (nm), have been shown to be the most effective for disinfection, although longer wavelength, less energetic UV can also disinfect if applied in much greater doses, there is concern for a bad case of sunburn. UVC wavelengths comprise photons (particles of light) that are the most energetic in the optical spectrum (comprising UV, visible, and infrared) and therefore are the most photochemically active.[4]

Ultraviolet (UV)-C radiation is a known disinfectant for air, water, and nonporous surfaces. UVC radiation has effectively been used for decades to reduce the spread of bacteria, such as tuberculosis. For this reason, UVC lamps are often called "germicidal" lamps. UV light exposure is a direct antimicrobial approach, and its effectiveness against different strains of airborne viruses has long been established. [5, 6] Principles of selective inactivation of viral genome.[5] UVC (100 to 280 nm)—are called 'germicidal' radiation because of its ability to kill bacteria and inactivate viruses.

UV light could not be used before because the spectrum of wavelengths emitted by a conventional mercury germicidal UV lamp is broad (200-400 nm). However, broad band UVC can cause injury to the skin (e.g. erythema, also known as sunburn) and eye (i.e. inflammation of the cornea or photokeratitis). There exists a more narrow wavelength window in the far-UVC region, between 200-230 nm (particularly around 207 to 222 nm wavelength), in which bacteria and viruses are efficiently deactivated, but which produces far less cytotoxic or mutagenic damage to human cells. While photons emitted in this range are absorbed to some degree by the nucleic acids of DNA/RNA, the principal factor in reducing infectivity is thought to result from absorption and resultant damage to proteins.

Far-UVC could not be used before because of less power to kill or deactivate microorganisms in a short time period. An augmented UVC chamber within a cartridge chamber isolates the insides of the augmentation chamber (a source of UVC). Isolation material that contains plastic material that is Polytetrafluorethylene (PTFE) will provide more than 95% reflectance (or Teflon® material where TEFLON is a registered trademark of Dupont Corporation). PTFE is naturally in white color but can be given different colors according to desire. As the performance of UVC LEDs increase, more microorganisms will be killed in a shorter period, in other words in milliseconds. The light distribution within an augmentation chamber (which may, for example, replace an N95 face mask filter) was modeled for different areas, and there may be at least 1 or 2 or 3 UVC LED's in the middle of the UVC augmentation chamber. UVC invisible light at 222 nanometers may be emitted from a selected diode and bounces off surfaces of walls within the UVC chamber and the UVC may spread throughout the interior chamber of an N95 mask, killing bacteria and deactivating viruses.

UVC radiation has been shown to destroy the outer protein coating of the SARS, which is a different virus from the current SARS-COVID-19 virus. UVC kills living bacteria, but viruses are technically not living organisms; thus, we should correctly say "inactivate viruses." Individual, energetic UV-C photons photochemically interact with the RNA and DNA molecules in a virus or bacterium to render these microbes non-infectious. This all happens on the microscopic level. Viruses are less than one micrometer (m, one-millionth of a meter) in size, and bacteria are typically 0.5 to 5 μm.[4] By contrast far-UVC light (207 to 222 nm) has been shown to be as efficient as conventional germicidal UV light in killing microorganisms [7], and studies to date suggest that these wavelengths at predetermined power levels do not cause any human health issues associated with direct exposure (such as sunburned skin) to conventional germicidal UV light.[8-10] Buonanno, M. et al., 207-*nm UV light-a promising tool for safe low-cost reduction of surgical site infections*.[8] UVC radiation can only inactivate a virus if the virus is directly exposed to the radiation.[11] There is some evidence that excimer lamps, with peak wavelength of 222-nm may cause less damage to the skin, eyes, and DNA than the 254 nm wavelength. UV-C penetrates only the superficial layers of the skin and eye, with the shortest wavelengths hardly penetrating at all to living cells (epidermis), so only a very mild, transitory "sunburn" (erythema) occurs from accidental over-exposure of skin areas. Even though germicidal GUV lamps can pose a theoretical delayed hazard, incidental UV exposures in the workplace would not significantly increase one's lifetime risk for developing a cataract of the eye or skin cancer when compared to daily exposure to the UV radiant energy in sunlight.[4]

In short, far-UVC light has a range in biological materials of less than a few micrometers, and thus it cannot reach living human cells in the skin or eyes, being absorbed in the skin stratum corneum or the ocular tear layer. But because viruses (and bacteria) are extremely small, far-UVC light can still penetrate and deactivate/kill them. Thus far-UVC light potentially has about the same highly effective germicidal properties of UV light, but without the associated human health risks.[8-10, 12] Specifically, far-UVC light (207-222 nm wavelength) is very strongly absorbed by proteins through the peptide bond, and other biomolecules. [13, 14] The molecular basis of biological effects of ultraviolet radiation and photoreactivation, is discussed in *Current topics in radiation research*, M. Ebert & A. Howard, Editors., North Holland Publishing Company: Amsterdam. p. 195-248 (1966).[14] So its ability to penetrate biological materials is very limited compared with, for example, 254 nm (or higher) conventional germicidal UV light. This limited penetration is still much larger than the size of viruses and bacteria, so far-UVC light is as efficient in killing these pathogens (such as the coronavirus) as conventional germicidal UV light.[8, 9, 12]

In a well-designed in-vitro study, Buonanno et al explored the efficacy of 222 nm wavelength light against two airborne human coronaviruses: alpha HCoV-229E and beta HCoV-OC43.[15] Both were isolated over 50 years ago and are endemic to the human population, causing 15-30% of respiratory tract infections each year.[16] Like SARS-CoV-2, the HCoV-OC43 virus is from the beta genus.[17] Buonanno et al showed that, for both alpha HCoV-229E and beta HCoV-OC43, exposure to 222-nm wavelength light reduced the expression of the viral spike glycoprotein as indicated by a reduction in green fluorescence.[18] Buonanno et al have shown that very low doses of far-UVC light efficiently kill airborne human corona viruses carried by aerosols. A dose as low as 1.2 to 1.7 mJ/cm2 of 222-nm wavelength UV light inactivates 99.9% of the airborne human coronavirus tested from both genera beta and alpha, respectively.[15] As all human coronaviruses have similar genomic size, a key determinant of radiation sensitivity, it is likely that far-UVC light will show comparable inactivation efficiency against other human coronaviruses, including COVID-19.

The severity of the COVID-19 pandemic warrants the rapid development and deployment of effective countermeasures to reduce person-to-person transmission. A promising approach uses single-wavelength far-UVC light at 222 nm wavelength generated by filtered excimer lamps, which inactivates airborne viruses without inducing biological damage in exposed human cells and tissue.[7, 10, 12, 19] The approach is based on the biophysically-based principle that far-UVC light, because of its very limited penetration in biological materials, can traverse and kill viruses and bacteria which are typically micrometer dimensions or smaller, but it cannot penetrate even the outer dead-cell layers of human skin, nor the outer tear layer on the surface of the human eye at predetermined power levels.

Figure 13:
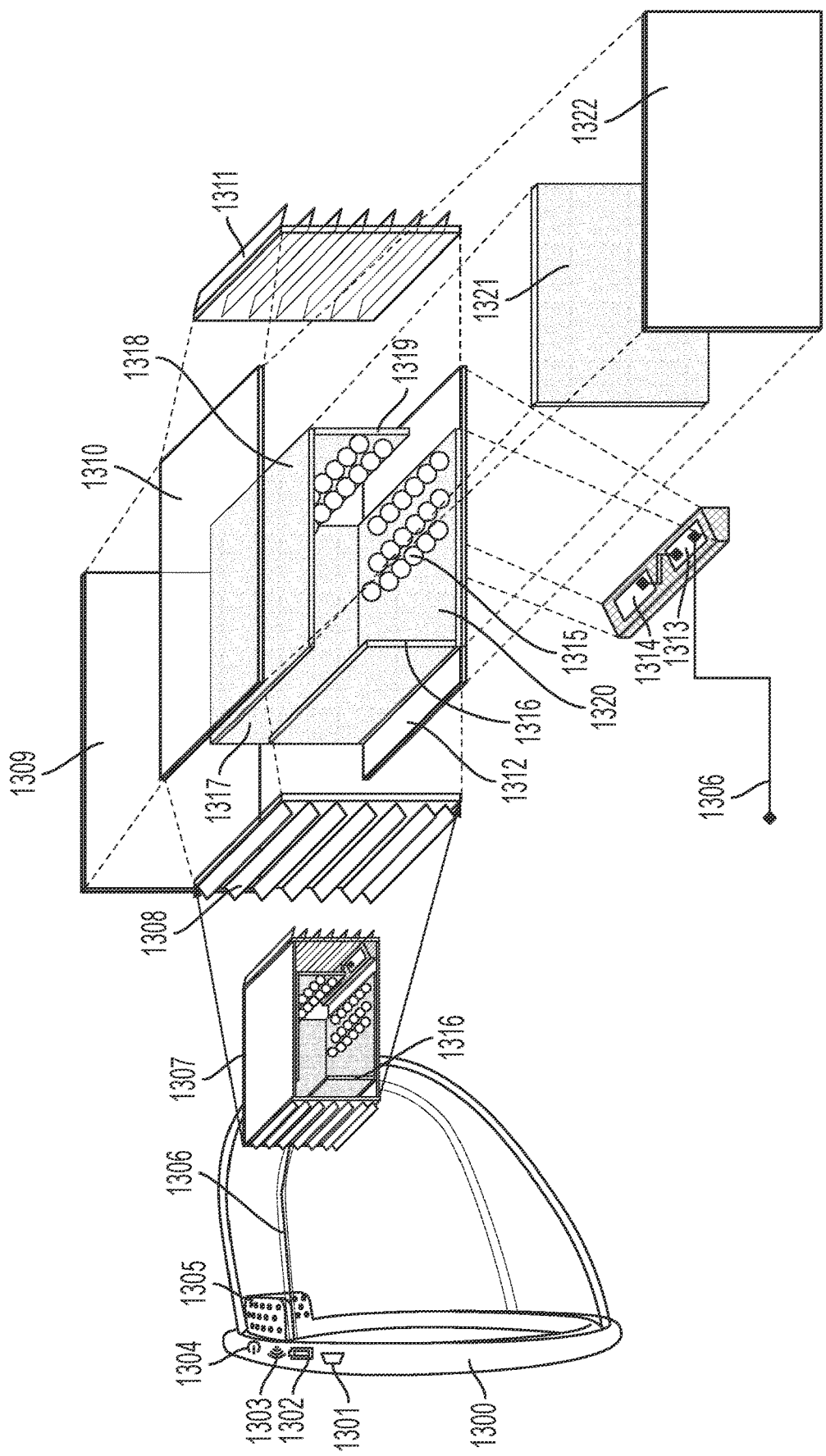
FIG. 13 demonstrates a lateral perspective and an expanded view of a soft silicone edged cushion 1300 for fitting to a user's face with a Ultraviolet-C(UVC)-cartridge 1307, i.e. ultraviolet light source at a wavelength between 207 and 222 nanometers that will not cause a user's skin to develop a sunburn condition but inactivates the virus so no virus escapes on exhale and is inactivated on inhale by a user. Cartridge 1307 may replace a typical particle filter of an N95 mask.
Figure 14:
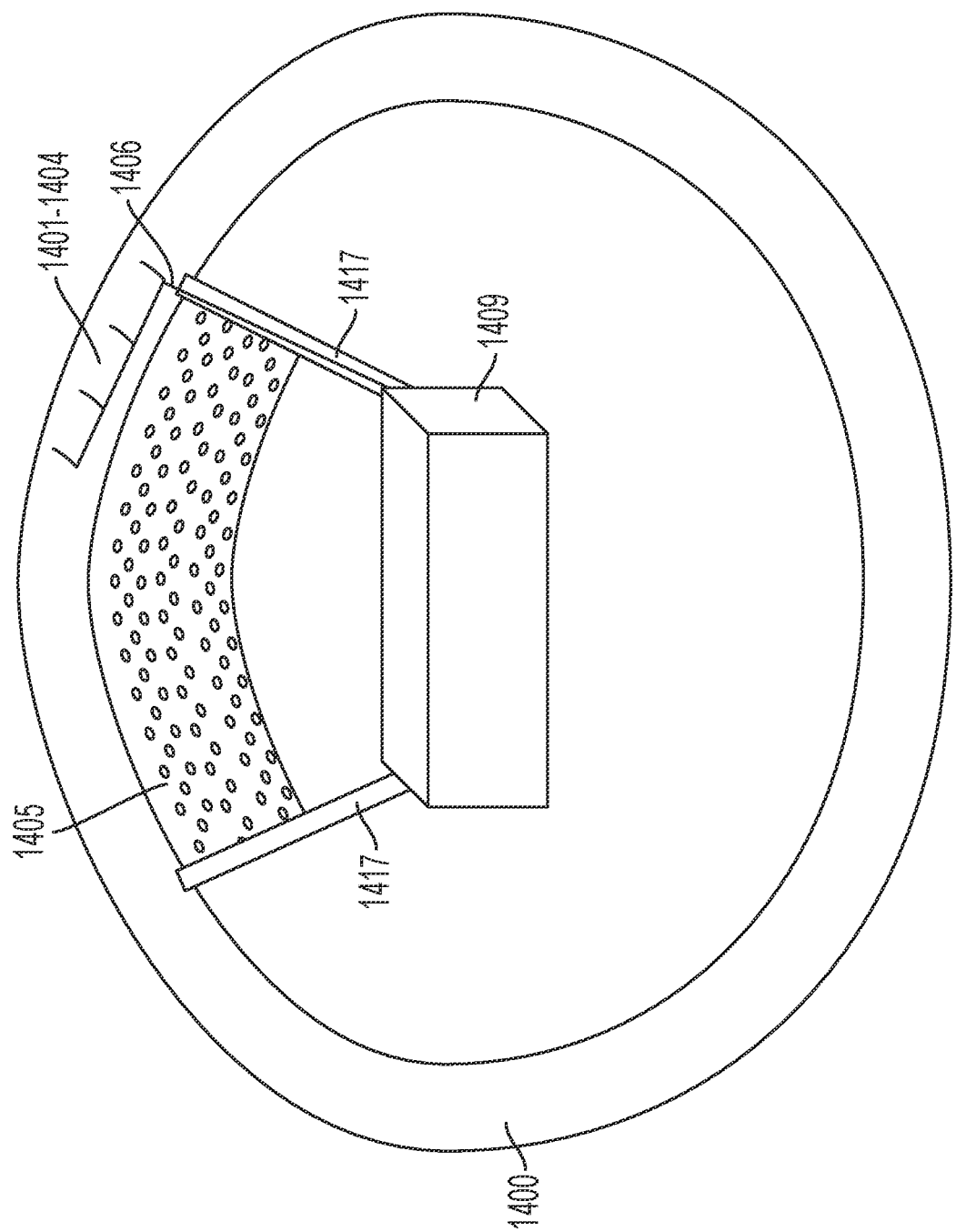
FIG. 14 displays rear view of soft silicone edged cushion 1400 for a wearer's face with UVC-cartridge 1409 which may replace a particle filter in an N-95 mask and be controlled by controls 1401-1404 located on the exterior edge of the cushion or on the cartridge 1409 which can be easily reached by the wearer of the face mask.

[8] The sensitivity of the coronaviruses to far-UVC light, together with extensive safety data even at much higher far-UVC exposures [7-10, 12, 20], suggests that it may be feasible and safe to have the lamps providing continuous low-dose far-UVC exposure on face masks, potentially reducing the probability of person-to-person transmission of coronavirus as well as other seasonal viruses such as influenza. In order to clarify UV limits, there are no regulatory UV radiation on indirect exposure limits. The American Conference of Governmental Industrial Hygienists publishes Threshold Limit Values (TLVs), which are recommended exposure limits.[21] Continuous far-UVC exposure in occupied public locations at the current regulatory exposure limit is −3 mJ/cm$^2$ (mW/cm$^2$).[21, 22]. For UV-C, TLV values are 250 mW/cm$^2$ at 180 nm and 3.1 mW/cm$^2$ at 275 nm. A TLV value for 222 nm is >3.1 mW/cm$^2$. A suggested dose level is <2.5 mW/cm$^2$ which is indirect UV. And this energy level will be delivered via a UVC cartridge 1307 having an augmentation box 1317,1319, 1321 (FIG. 13) within or a cartridge 1307 (FIG. 13) or 1409 (FIG. 14). The energy will not be directed to the skin or the eye (cornea) due to the several reflective surfaces of the augmentation box interior and the boundary set by using a cushion according to the present invention of FIGS. 5A to 10B.

The present invention may comprise a "UVC-cartridge" directed to a "socket" specifically designed for replacing a filter cartridge in a face mask such as an N95 face mask or other PPE. Referring briefly to FIG. 13, the UVC cartridge 1307 is shown which may extend from the front side of, for example, an N95 mask to the rear side of an N95 mask. UVC cartridge 1307 is responsible for inhalation/exhalation of air by a mask wearer and is seen having louvered front and rear sides 1311, 1308 respectively. In an expanded view of UVC cartridge 1307, the cartridge comprises six sides: rear side 1308, front side 1311, top wall 1310, right side wall 1309, left side wall 1322 and bottom 1312. Inside the UVC cartridge 1307 is an augmentation box comprising rear wall 1316 also seen in expanded view comprising six sides: rear wall 1316 which may be ½ to ¾ the height, preferably ⅔ the height of cartridge rear side 1308; front wall 1319 which may be ½ to % the height, preferably ⅔ the height of cartridge front side 1311, right side 1317, left side 1321, top 1318 and bottom 1320. Located between front wall 1319 and front side 1311 is a six sided box (unlabeled) containing a microelectronic circuitry board 1313 for a filtered Krypton-Chloride 222 nm wavelength ultraviolet light emitting diode and an associated battery circuit 1314 and sets on cartridge bottom 1312. A UVC-cartridge 1307 will include one or more UVC-LEDs (lamp), UVC augmentation material (preferably PTFE but there are other materials e.g. aluminum, steel, bora silica) that may reflect UV, the battery 1314 (preferably a chargeable lithium type battery), microelectronic circuitry 1313 (may include a microelectronic circuit, transistor, condenser, light emitting diode(s) and a miniature cooling fan) and a cable 1306 to controls 1301 through 1304 comprising an on-off button 1304, Bluetooth indicator 1303, charging indicator display 1302, and a charging micro-port 1301 (for insertion of a charger (for example, a standard USB interface similar to that of a USB computer)) for charging, for example, the lithium battery which are shown located on cushion 1300. Bluetooth indicator light 1303 indicates to a mask wearer that Bluetooth telecommunications service is available in vicinity of the mask wearer. Components 1301 through 1304 may also be located at the front of cartridge top wall 1310 (not shown) or at the front of either of the cartridge side walls 1309, 1322 Thus, the circuitry 1301 to 1304 may comprise a portion of the cushion or the front of the cartridge and may, along with the UV source, comprise a component of a filter/bacteria killer/virus deactivator replacing a customary filter of an N95 mask, for example, or for use in other PPE. Besides a face mask, a UVC-cartridge 1307 can also be used in a "Powered Air-Purifying Respirator" (a hooded device with a backpack UV source) and in oxygen and ventilator masks.

A socket may be fixed to the face mask or other PPE and may be used for holding a UVC-cartridge 1307, for example, as a replacement for a known air filter. Socket material will be similar to that of the UV-cartridge 1307 and may be made of plastic. Reflective walls within the cartridge and augmentation box will diffuse the UVC so that it kills bacteria and deactivates viruses within a face mask and other PPE and when inhaled/exhaled through the cartridge. When the mask needs to be cleaned, the socket and UVC-cartridge will be detached from each other by a suitable connector (plug/jack not shown), for example, located at the cushion end of a cable 1306 to the cushion or the side and top walls 1309, 1310, 1322 with sufficient wires for the on/off button, battery level display, USB port and Bluetooth indicator. After cleaning or charging, re-insertion and re-use of the UVC-cartridge 1307 may be performed. A frame of a UVC-cartridge 1307 may comprise impact resistant plastic material and sealed with a UV-blocker material (e.g. UV-blocker paint). The size of a cartridge 1307 may vary from 30 cm$^2$ to 100 cm$^2$, for example, measure 6 cm by 3 cm by 3 cm or 54 cm$^3$. In this case, approximately 25 mW/cm$^2$ or less power of UVC (below cell phone emission levels) is used which is not hazardous to one's eyes or skin. Given a typical surface area of an N95 face mask or a typical rectangular face mask or other PPE covering mouth and nose and not covering face and eyes, this translates to 450 mW/hour at maximum power level.

Figure 11B:
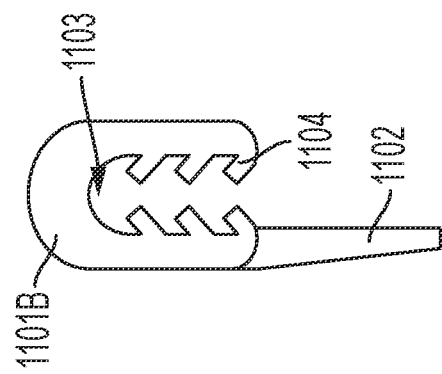
FIG. 11B shows dimensions a side cut view, such that the soft U-shaped medical silicone section 1101B clasps the mask at its lateral edge 1050 (not shown).
Figure 11A:
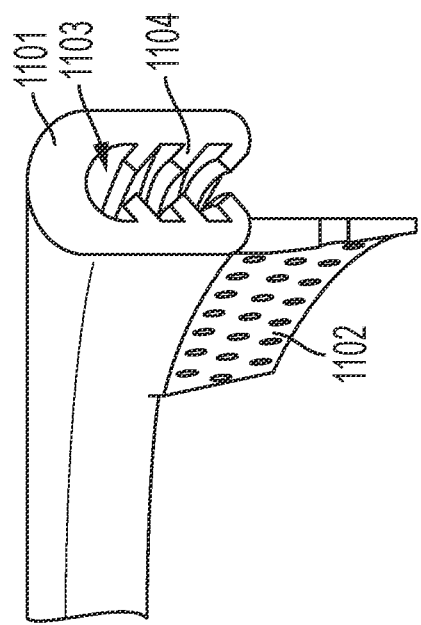
FIG. 11A shows in cross-section (lateral edge 1050 of mask not shown) with 3-protrusions 1104 inside a serrated gap 1103 for clasping a mask lateral edge and a nose extension 1102.

FIG. 11A shows in cross-section and perspective view a cushion design of the present invention for clasping a lateral edge of the mask 1050. A U-shaped channel may have 3-protrusions 1104 inside a serrated gap 1103 in a U-shaped channel cross-section with grasping teeth 1104. A soft U-shaped silicone 1101 for clasping the lateral edges of the mask 1104 is continuous and is manually fitted to the lateral edges of the mask 1050 by the strength of the teeth protrusions and the depth of the gap. Reference numeral 1103 represents the continuity of the serrated gap and under soft silicone. Reference numeral 1102 represents a soft silicon bridge for protecting the nasal area of a user. Silicon bridge 1102 may be located under nose bridge 410, for example, to prevent itching. Bridge 1102 may be made porous to provide lesser weight and sweating in the nose area. FIG. 11B shows FIG. 11A in cross-section. Typical dimensions in FIG. 11B are 10 mm for the width of cushion 1101B and length with three protrusions 15 mm. The spacing between protrusions 1104 should by sized to match the width of lateral edges of a face mask, for example, between 1 and 2 mm. The length of a nose bridge 1102 may be between 10 and 15 mm or, preferably, 12 mm.

Figure 12B:
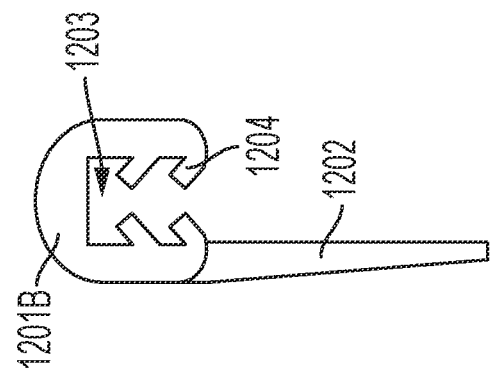
FIG. 12B shows the cross-section 1201B, such that the soft U-shaped medical silicone section 1030 clasps the mask at lateral edge 1050 (not shown).
Figure 12A:
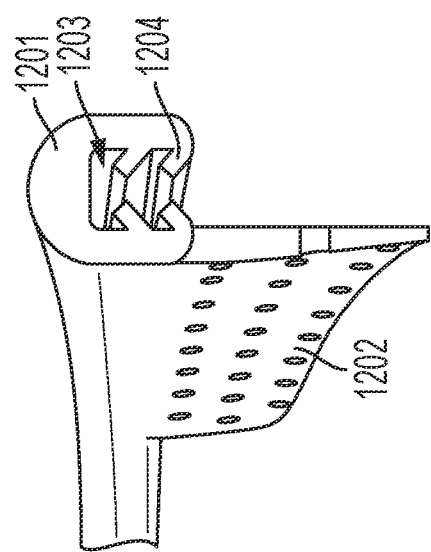
FIG. 12A shows cushion 1201 in cross-section perspective view at a lateral edge of the mask 1050 with 2-protrusions 1204 inside serrated gap 1203.

FIG. 12A shows in cross-section/perspective view at a lateral edge of the face mask, for example, mask 1050 with just 2-protrusions 1204 inside the serrated gap 1203 for grasping face mask lateral edges. Even more grasping teeth than three protrusions may be provided but are believed to be not necessary to grasp a cloth or plastic edge of a face mask, ventilator mask or other PPE. FIG. 11A and FIG. 12A are almost the same except they have 3 and 2 protrusions respectively inside of serrated gaps 1103, 1203, respectively. A range of protrusions or teeth may be between one and four protrusions. FIG. 12B shows a cross-section 1201B of the cushion of FIG. 12A. Dimensions are proportionately smaller that for FIG. 11B because only two protrusions 1204 are used to clasp face mask lateral edges.

FIG. 13, already described in some detail above, demonstrates a lateral view and an expanded view of a soft silicone edged cushion 1300 for one's face mask with a UVC-cartridge 1307, i.e. ultraviolet light source at, for example, far UVC wavelength. Reference numeral 1300 depicts a soft silicone edged cushion that clasps a lateral edge of a face mask (not shown). Reference numeral 1301 shows a micro-port entrance for USB power for battery charging purposes or data purposes. Reference numeral 1302 shows a battery level indicator for, for example, a lithium battery or other rechargeable battery. Reference numeral 1303 represents a Bluetooth display. An on-off button is shown as numeral 1304 for turning battery power on and off. Reference numeral 1305 is a porous silicon bridge for the nasal area, preferably light weight. Reference numeral 1306 shows electric cable between buttons and UVC-cartridge 1307 through at least one support (four supports shown) for cartridge 1307. Reference numeral 1307 represents a UVC-cartridge box in total. Reference numeral 1307 has 6-sides as a cube or elongated box. Four sides of the cartridge box in expanded view may be completely covered, for example, with a lightweight plastic external material. The remaining two sides comprise a back (reference numeral 1308) and a front side (reference numeral 1311) panels of cartridge 1307 which will be semi-opened, for example, at a 30-degree to 75-degree angle (preferably a 45° angle opening). Reference numeral 1307 is, for example, a plastic cartridge box which has all electronic components inside of it including power on/off, battery, charger and other components which may be located as buttons/displays alternatively on or embedded in the cushion within reach of the user or on the cartridge 1307 front top side 1310 (or front of side walls 1309, 1322, controls not shown). Reference numeral 1308 represents a back panel facing a wearer's face (for example, 45 degree opened angle) of UVC-cartridge box 1307. UVC augmentation box coated with Polytetrafluoroethylene (PTFE material) may be inside of UVC-cartridge box and smaller in size than UVC-cartridge box 1307. UVC augmentation box may have 6-sides. A lower one-third (range of ¼ open to ¾ open) of front panel (reference numeral 1316) and an upper one-third of back panel (reference numeral 1316) will be open for air circulation through angled front and back panels 1308 and 1311. Reference numeral 1317 demonstrates one side wall of a UVC cartridge coated with PTFE material, which is commonly used as a non-stick surface and is well-known as Teflon in the world but has other common names as well (see Wikipedia "PTFE"). The augmentation box having side wall 1317 may contain a plurality of walls and surfaces so coated with PTFE to augment the UVC selected wavelength between 200 and 230 nm and release the augmented invisible U/V light from the cartridge through an open window to fill the face mask. Reference numeral 1319 represents a top outer side of roof 1318 of augmentation box (lower ⅓ of 1319 is open as described earlier and within a range of ¼ open to % open) comprising part of side wall 1317, roof of augmentation box 1318, inner side wall 1321 of roof 1318, outer side wall of augmentation box and mini UV lamps 1315. Reference numeral 1311 shows the front panel (45 degree opened angle) of the expanded UVC-cartridge box 1307. Reference numeral 1320 demonstrates the bottom inner side of the cartridge box 1307 coated with PTFE material. Reference numerals 1313 and 1314 are located in a six-sided box of bottom side 1312. Reference numeral 1313 may be a microelectronic circuitry board such as for a filtered Krypton-Chloride 222 nm wavelength or, shortly, a Care222 filtered far UV-C excimer lamp module manufactured by USHIO America of Cypress, Calif. Reference numeral 1314 represents the battery, for example, a lithium battery or other source of power. The power of the system, for example, will be a lithium battery and in the range of 200 to 1000 mAh (milli Ampere hours) (located either on the U-shaped cushion 1300 or the plastic box). Reference numeral 1315 demonstrates UV lamps, up to 50 (fifty) light emitting micro-LEDs may be used in a nanotechnology environment in order to generate enough power to kill bacteria and deactivate viruses. The micro-LED's 1315 may also be located on top outer side 1319. Reference numeral 1316 represents an inner side of augmentation box (upper ⅓ of 1316 is open as described earlier). Reference numeral 1317 represents a rear side wall of the augmentation box. Reference numeral 1318 represents the roof of the augmentation box. Reference numeral 1321 represents the inner side wall of the augmentation box. Reference numeral 1320 represents the floor of the augmentation box. Reference numeral 1319 represents the forward side of the augmentation box while reference numeral 1322 represents the outer wall of the cartridge joined to bottom 1312 and top 1310 of cartridge 1307.

The value of UVC power appropriate for deactivating virus and preserving skin from sunburn is a very complex issue. First, one should calculate the fluence rate (UV dosage) distribution within the UV cartridge. A computer program takes into consideration the cartridge size, the reflective material used and determine a volume average of the UV dose rate over the entire cartridge. The residence time of air in the cartridge is given by a volume of inhalation and exhalation (volume/flow rate). The UV dose is then the product of the average UV dose rate and the residence time. How and where to measure irradiance is important since reflectors may focus or diffuse UV energy. Geometry of the reflectors and their material as well as the geometry of the reflector placement are factors.

FIG. 14 displays a rear view of a soft silicone edged cushion 1400 for a face mask or other PPE with a UVC-cartridge 1409. Reference numeral 1400 (or 1300) depicts a soft silicone edged cushion. Reference numerals 1401-1404 are cushion 1400 buttons/displays and controls 1301 through 1304. Supports 1417 may support nose bridge 1405 and carry cable 1406 between soft silicone edged cushion 1400 and UVC-cartridge 1409. Reference numeral 1405 (similarly as 1305) shows a silicon bridge for the nasal area. Reference numeral 1406 (similarly as 1306) shows electric cable connection between buttons/displays and controls 1401 to 1404 which may be alternatively located on the top front or fronts of sides of UVC-cartridge 1409, shown to be larger than cartridge 1307 shown in FIG. 13. FIG. 14 may be designed differently, for example, nose bridge 1405 may be alternatively perforated with squares or comprise a soft, durable netting.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present invention in any way which should be limited only by the claims which follows.

REFERENCES

[1] https://www.worldometers.info/coronavirus/.
[2] https://www.worldometers.info/coronavirus/-countries.

[3] Bai Y, Yao L, Wei T, Tian F, Jin D Y, Chen L, Wang M. Presumed Asymptomatic Carrier Transmission of COVID-19. JAMA. 2020 Apr. 14; 323(14):1406-1407.
[4] https://media.ies.org/docs/standards/IES-CR-2-20-V1-6d.pdf.
[5] Budowsky, E. I. et al. Principles of selective inactivation of viral genome. I. UV-induced inactivation of influenza virus. Arch. Virol. 68(3-4), 239-47 (1981).
[6] Kowalski, W. J. Ultraviolet Germicidal Irradiation Handbook: UVGI for Air and Surface Disinfection. New York: Springer, (2009).
[7] Narita, K. et al. 222-nm UVC inactivates a wide spectrum of microbial pathogens. J Hosp Infect (2020).
[8] Buonanno, M. et al. 207-nm UV light-a promising tool for safe low-cost reduction of surgical site infections. II: In-Vivo Safety Studies. PLoS One 11(6), e0138418 (2016).
[9] Buonanno, M. et al. Germicidal efficacy and mammalian skin safety of 222-nm uv light. Radiat. Res. 187(4), 483-491 (2017).
[10] Ponnaiya, B. et al. Far-UVC light prevents MRSA infection of superficial wounds in vivo. Plos One 13(2), e0192053 (2018).
[11] https://www.fda.gov/medical-devices/coronavirus-covid-19-and-medical-devices/uv-lights-and-lamps-ultraviolet-c-radiation-disinfection-and-coronavirus.
[12] Buonanno, M. et al. 207-nm UV light—a promising tool for safe low-cost reduction of surgical site infections. I: in vitro studies. Plos One 8(10), e76968 (2013).
[13] Goldfarb, A. R. & Saidel, L. J. Ultraviolet absorption spectra of proteins. Science 114(2954), 156-7 (1951).
[14] Setlow, J. The molecular basis of biological effects of ultraviolet radiation and photoreactivation, in Current topics in radiation research, M. Ebert & A. Howard, Editors., North Holland Publishing Company: Amsterdam. p. 195-248 (1966).
[15] Buonanno M, Welch D, Shuryak I, Brenner D J. Far-UVC light (222 nm) efficiently and safely inactivates airborne human coronaviruses. Sci Rep. 2020 Jun. 24; 10(1):10285.
[16] Fehr, A. R. & Perlman, S. Coronaviruses: an overview of their replication and pathogenesis. Methods Mol. Biol. 1282, 1-23 (2015).
[17] Woo, P. C. et al. Coronavirus genomics and bioinformatics analysis. Viruses 2(8), 1804-20 (2010).
[18] Trevisan, A. et al. Unusual high exposure to ultraviolet-C radiation. Photochem. Photobiol. 82(4), 1077-9 (2006).
[19] Yamano, N. et al. Long-term effects of 222 nm ultraviolet radiation C sterilizing lamps on mice susceptible to ultraviolet radiation. Photochem Photobiol, (2020).
[20] Narita, K. et al. Chronic irradiation with 222-nm UVC light induces neither DNA damage nor epidermal lesions in mouse skin, even at high doses. PLoS One 13(7), e0201259 (2018).
[21] https://www.unr.edu/ehs/program-areas/radiation-safety/ultraviolet.
[22] https://www.med.navy.mil/sites/nmcphc/Documents/policy-and-instruction/ih-ultraviolet-radiation-technical-guide.pdf.

What is claimed is:

1. A cushion apparatus comprising a soft medical gel for use with a face mask, the apparatus for clasping lateral edges of the face mask when formed to have a circumference approximately the size of the face mask, the cushion apparatus comprising:

a soft medical silicone cushion shell formed into a U-shape channel cross-section, the one U-shape channel cross-section having a predetermined circumference for fitting and clamping one of cloth, plastic and composite material lateral edges of the face mask, a softer silicone gel or a petroleum jelly for coating the cushion proximate a wearer and to seal lateral edges of the face mask clamped by the U-shaped channel, the gel or jelly promoting comfort to a wearer of the face mask and preventing the lateral edges of the face mask from leaking exhaled air to an exterior of the face mask, and the face mask comprising an ultraviolet emitting cartridge module containing an augmentation module for treating air inhaled/exhaled by a user by emitting ultraviolet light of predetermined wavelength and predetermined dose level for directly deactivating a viral pathogen within the face mask and not causing skin damage when the face mask is worn, either the cartridge module or the augmentation module having one of a lead cable to three of an on/off button, a battery, a Bluetooth indicator, and a USB battery charging port, the silicone cushion shell containing the three of the on/off button, the battery, the Bluetooth indicator, and the USB battery charging port, the USB battery charging port for receiving power for charging the battery.

2. The soft shell cushion apparatus comprising the soft medical gel as recited in claim 1, the cushion apparatus comprising medical silicone gel or jelly of a Shore A hardness value between a value of 0 and 80.

3. The soft shell cushion apparatus comprising the soft medical gel as recited in claim 1, the soft medical silicone cushion shell gel having a Shore A hardness value between 10 and 40.

4. The soft shell cushion apparatus comprising the soft medical gel as recited in claim 1, the apparatus adapted for use with an N95 face mask having a predetermined cloth or hardened paper material lateral edge of predetermined circumference, the soft shell cushion apparatus further comprising: a plastic nose bridge for attachment to a foam rubber nose bridge of the N95 mask, the plastic nose bridge formed into one of a U-shape and a shape of the foam rubber nose bridge, the plastic nose bridge adapted to clasp to the foam rubber nose bridge of an interior of the N95 mask, the plastic nose bridge for attachment to the foam rubber nose bridge being of predetermined length and deformable material to be deformed to protect the bridge of a nose of a wearer of the mask and adapted to be coated with a soft medical silicone gel or a petroleum jelly to prevent the escape of air from above the nose and to protect the nose from abrasion.

5. The soft shell cushion apparatus comprising the soft medical gel as recited in claim 4, the soft shell cushion apparatus being adapted for self-installation by a wearer of the N95 face mask to clasp the lateral edge of the N95 face mask.

6. A method of manufacture of soft shell cushion apparatus containing one of a soft gel, air or hydrogen under pressure for forming an installable fit to a face mask comprising the steps of:

measuring a length or circumference of a lateral edge surrounding a given face mask, forming a U-shaped channel of the measured length of medical grade silicone having an extra soft Shore A Hardness scale value between 10 and 40, the predetermined length being determined by measuring a circumference of lateral edges of the given face mask using injection molding, forming a compartment of the measured length, the compartment for containing one of soft gel, air and hydrogen, filling the U-shaped channel with medical grade silicone having an extra soft Shore A Hardness scale value between 1 and 10, air or hydrogen under pressure, one of silicone, air and hydrogen filling the measured length of U-shaped channel, using one of a tapered end of the U-shaped channel of the measured length or circumference, a plug, heat and a bonding material for one of fitting and forming two ends of the U-shaped channel of the measured length or circumference together by joining one end to the other after the filling to join the ends of the U-shaped channel together to comprise a sealed loop for installation to the face mask, and fixing a socket to the face mask for holding an ultraviolet light cartridge, the ultraviolet light cartridge having a source of ultraviolet light having a predetermined wavelength and a predetermined dose level of ultraviolet light, the ultraviolet light for directly deactivating a viral pathogen within the face mask.

7. The soft shell cushion apparatus of claim 1 wherein the predetermined wavelength of ultraviolet light is between 207 and 222 nanometers and the predetermined dose level is less than 2.5 mW/cm$^2$.

8. The soft shell cushion apparatus of claim 1 wherein the augmentation module comprises isolation material of one of Polytetrafluorethylene and TEFLON material.

9. The soft shell cushion apparatus of claim 1 wherein the augmentation material comprises a plurality of reflective surfaces, the reflective surfaces comprising one of Polytetrafluorethylene, TEFLON material, aluminum, steel and bora silica that reflect ultraviolet light.

10. The soft shell cushion apparatus of claim 1 wherein the augmentation module comprises an excimer lamp with a peak wavelength of 222 nanometers.

11. The method of manufacture of soft shell cushion apparatus as recited in claim 6 wherein the predetermined wavelength is between 200 and 230 nanometers.

12. The method of manufacture of soft shell cushion apparatus as recited in claim 6 wherein the predetermined dose level is less than 2.5 mW/cm$^2$.

13. The method of manufacture of soft shell cushion apparatus as recited in claim 6 wherein the ultraviolet light cartridge comprises isolation material of Polytetrafluorethylene.

* * * * *